United States Patent
Elmaanaoui

(10) Patent No.: US 11,980,443 B2
(45) Date of Patent: May 14, 2024

(54) DEVICES, SYSTEMS, AND METHODS FOR IMAGE SYNCHRONIZATION IN INTRACORONARY IMAGING

(71) Applicant: Canon U.S.A., Inc., Melville, NY (US)

(72) Inventor: Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 277 days.

(21) Appl. No.: 17/378,476

(22) Filed: Jul. 16, 2021

(65) Prior Publication Data

US 2023/0015390 A1 Jan. 19, 2023

(51) Int. Cl.
*A61B 5/00* (2006.01)

(52) U.S. Cl.
CPC .......... *A61B 5/0084* (2013.01); *A61B 5/0066* (2013.01); *A61B 5/0071* (2013.01)

(58) Field of Classification Search
CPC ... A61B 5/0059; A61B 5/0066; A61B 5/0071; A61B 5/0082; A61B 5/0084
See application file for complete search history.

(56) References Cited

U.S. PATENT DOCUMENTS

| | | | |
|---|---|---|---|
| 8,049,900 B2 | 11/2011 | Kemp et al. | |
| 8,395,781 B2 | 3/2013 | Kemp et al. | |
| 8,412,312 B2 | 4/2013 | Judell et al. | |
| 9,007,696 B2 | 4/2015 | Petersen et al. | |
| 9,526,424 B2 | 12/2016 | Judell | |
| 11,259,702 B2 | 3/2022 | Yamada | |
| 11,382,516 B2 | 7/2022 | Wu et al. | |
| 2004/0054270 A1 | 3/2004 | Pewzner et al. | |
| 2019/0059734 A1 | 2/2019 | Yamada | |
| 2020/0297414 A1 | 9/2020 | Flanagan | |
| 2020/0390323 A1 | 12/2020 | Yamada | |
| 2021/0174125 A1 | 6/2021 | Zhang | |
| 2022/0040402 A1 | 2/2022 | Elmaanaoui | |
| 2022/0042781 A1 | 2/2022 | Yamada | |
| 2022/0044396 A1 | 2/2022 | Athanasiou | |
| 2022/0044428 A1 | 2/2022 | Elmaanaoui | |

(Continued)

FOREIGN PATENT DOCUMENTS

| | | |
|---|---|---|
| JP | 2020-532369 A | 11/2020 |
| WO | 2020257619 A1 | 12/2020 |
| WO | 2021055837 A1 | 3/2021 |

OTHER PUBLICATIONS

Qi, Ji, et al. "Aggregation-induced emission luminogen with near-infrared-II excitation and near-infrared-I emission for ultradeep intravital two-photon microscopy." ACS nano 12.8 (2018): 7936-7945.*

(Continued)

*Primary Examiner* — Carolyn A Pehlke
(74) *Attorney, Agent, or Firm* — Canon U.S.A., Inc. IP Division

(57) ABSTRACT

Devices, systems, and methods perform operations that include the following: obtaining a reflectance-detection signal from a back-reflected-light detector, wherein the back-reflected-light detector is configured to detect back-reflected excitation light and generate the reflectance-detection signal based on the back-reflected excitation light; determining whether blood clearance has been achieved based on the reflectance-detection signal; and issuing a clearance indicator in response to determining that blood clearance has been achieved.

20 Claims, 14 Drawing Sheets

(56) References Cited

U.S. PATENT DOCUMENTS

| | | |
|---|---|---|
| 2022/0104786 A1 | 4/2022 | Kunio |
| 2022/0218205 A1 | 7/2022 | Brushett |
| 2022/0346885 A1 | 11/2022 | Kunio |
| 2023/0015390 A1 | 1/2023 | Elmaanaoui |
| 2023/0181016 A1* | 6/2023 | Ughi .................... A61B 5/0066 600/109 |

OTHER PUBLICATIONS

European Patent Office, Search Report and Search Opinion, Application No. 22185135.5, dated Dec. 16, 2022.
Japanese Patent Office, Notice of Reasons for Refusal, Japanese Patent Application No. 2022-114644, dated Oct. 17, 2023.

* cited by examiner

DEVICES, SYSTEMS, AND METHODS FOR IMAGE SYNCHRONIZATION IN INTRACORONARY IMAGING

BACKGROUND

Technical Field

This application generally concerns devices, systems, and methods that perform medical imaging.

Background

Fiber-optic imaging devices and endoscopes enable the imaging of internal tissues and organs. For example, in cardiology, an optical-imaging device that is capable of optical coherence tomography (OCT) may be used to acquire depth-resolved images of a sample (e.g., tissues, organs). The optical-imaging device, which may include a sheath, a coil, and an optical probe, may be navigated through a lumen (e.g., a vessel) or a cavity.

Optical coherence tomography (OCT) is a technique for obtaining high-resolution cross-sectional images of samples, and enables real time visualization. OCT techniques measure the time delay of light by using an interference optical system or interferometry, for example through the use of Fourier Transform interferometers or Michelson interferometers. A light from a light source is split into a reference arm and a sample (or measurement) arm by a splitter (e.g., a beamsplitter). A reference beam is reflected from a reference mirror (partially reflecting or other reflecting element) in the reference arm, while a sample beam is reflected or scattered from a sample in the sample arm. Both beams combine (or are recombined) at the splitter and generate interference patterns. The output of the interferometer is detected with one or more detectors (e.g., photodiodes, multi-array cameras) in one or more devices, for example a spectrometer (e.g., a Fourier Transform infrared spectrometer). The interference patterns are generated when the path length of the sample arm matches that of the reference arm to within the coherence length of the light source. By evaluating the output beam, a spectrum of input radiation may be derived as a function of frequency. The frequency of the interference patterns corresponds to the distance between the sample arm and the reference arm. The higher the frequencies are, the greater the differences of the path lengths are. Single mode fibers are commonly used for OCT optical probes, and double clad fibers are also commonly used for fluorescence and spectroscopy.

Spectrally encoded endoscopy (SEE) is an endoscopy technology that uses a broadband light source, a rotating or oscillating grating, and a spectroscopic detector to encode spatial information from a sample. When illuminating light to the sample, the light is spectrally dispersed along one illumination line, such that the dispersed light illuminates a specific position of the illumination line with a specific wavelength. When the reflected light from the sample is detected with a spectrometer, the intensity distribution is analyzed as the reflectance along the line where the wavelength encodes the spatial information. By rotating or oscillating the grating to scan the illumination line, a two-dimensional image of a sample is obtained.

In order to acquire cross-sectional images of lumens (e.g., vessels, bronchi) and cavities (e.g., nasal cavities), the optical probe is rotated with a fiber-optic rotary joint (FORJ). A FORJ is the interface unit that operates to rotate one end of a fiber or optical probe. In general, a free space beam coupler is assembled to separate a stationary fiber and a rotor fiber inside the FORJ. And the optical probe may be simultaneously translated longitudinally during the rotation so that helical-scanning pattern images are obtained. This translation is most commonly performed by pulling the tip of the probe back along a guidewire towards a proximal end and is, therefore, referred to as a pullback.

A multi-modality system, such as an OCT, fluorescence, and spectroscopy system, with an optical probe is developed to obtain multiple types of information at the same time. The multi-modality FORJ has a beam combiner for at least two beams with multiple wavelengths to couple into the probe. Generally, lenses are assembled to make collimated beams for both stationary and rotor fibers in the beam combiner. Further, the detected light may be collected in the same or in one or more additional fibers, and, if rotating, these additional fibers may structurally interfere with each other.

SUMMARY

Some embodiments of a medical-imaging system comprise a back-reflected-light detector that is configured to detect back-reflected excitation light and generate a reflectance-detection signal based on the back-reflected excitation light; one or more computer-readable media storing instructions; and one or more processors that are in communication with the one or more computer-readable media. Also, when executing the instructions, the one or more processors cooperate with the one or more computer-readable media to perform operations that comprise determining whether blood clearance has been achieved based on the reflectance-detection signal, and in response to determining that blood clearance has been achieved, sending, to a pullback unit, an instruction to begin a pullback procedure.

Some embodiments of a device for detecting blood clearance comprise one or more electrical circuits that are configured to perform operations that comprise the following: obtaining a reflectance-detection signal from a back-reflected-light detector, wherein the back-reflected-light detector is configured to detect back-reflected excitation light and generate the reflectance-detection signal based on the back-reflected excitation light; determining whether blood clearance has been achieved based on the reflectance-detection signal; and issuing a clearance indicator in response to determining that blood clearance has been achieved.

Some embodiments of a method for medical imaging comprise obtaining a reflectance-detection signal that was generated based on back-reflected excitation light; determining whether blood clearance has been achieved based on the reflectance-detection signal; and in response to determining that blood clearance has been achieved, issuing a clearance indicator.

DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or."

Figure 1:
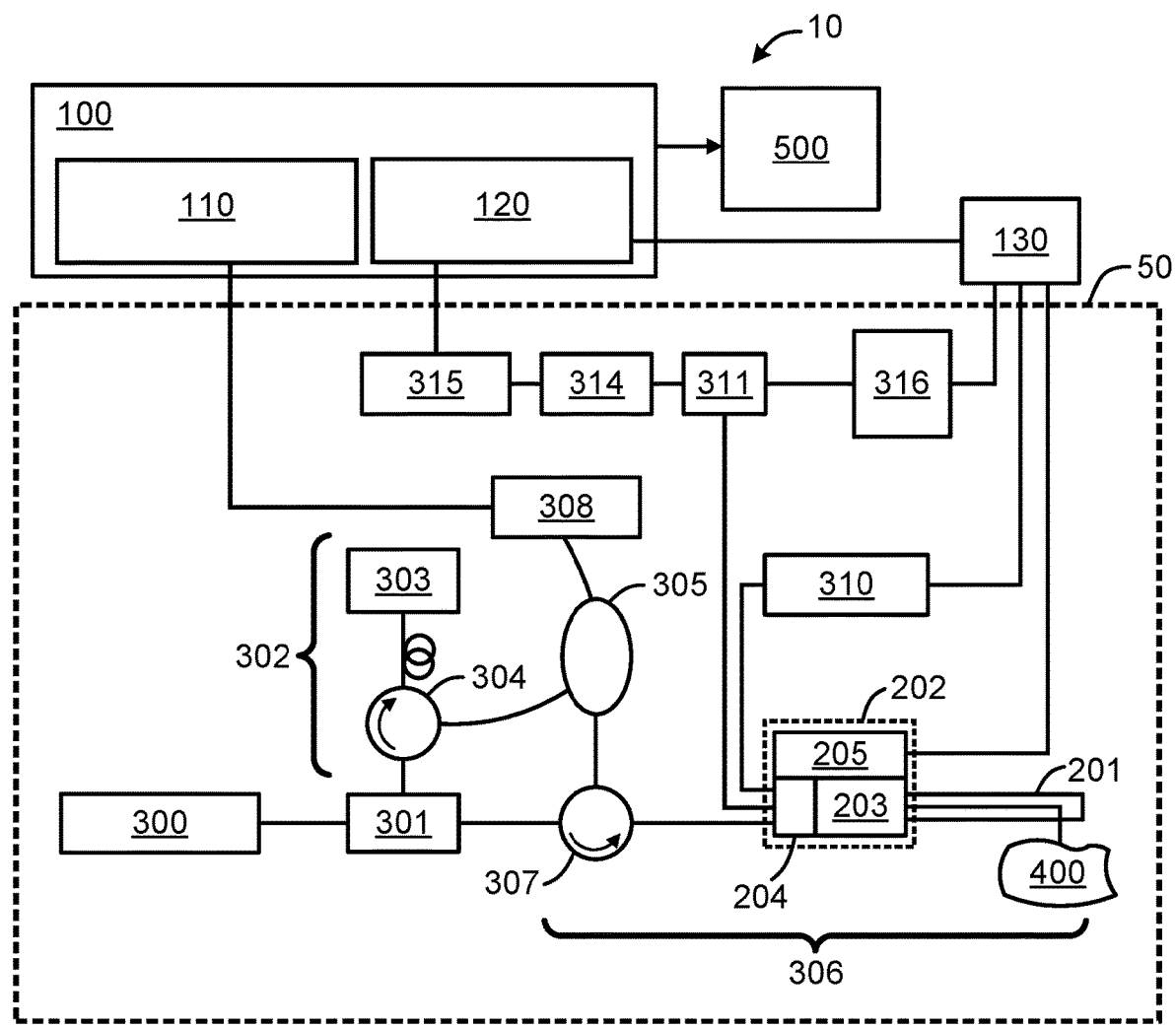
FIG. 1 illustrates an example embodiment of a medical-imaging system.

FIG. 1 illustrates an example embodiment of a medical-imaging system. The medical-imaging system 10 includes an imaging subsystem 50; an imaging station 100, which is a specially-configured computing device (e.g., desktop, laptop, server, workstation); and a blood-clearance monitor 130. The imaging subsystem 50 includes an optical-imaging device 201, a patient interface unit (PIU) 202, an OCT-light source 300, a splitter 301, a mirror 303, a first circulator 304, an OCT combiner 305, an OCT detector 308, a second circulator 307, an excitation-light source 310, a dichroic filter 311, a line filter 314, a fluorescence detector 315, and a reflectance detector 316.

This embodiment of the medical-imaging system 10 is a multi-modal optical coherence tomography (MMOCT) system (e.g., a multi-modality swept-source OCT system). Although this embodiment of the medical-imaging system 10 can perform both OCT imaging and fluorescence imaging (e.g., auto-fluorescence imaging, near-infrared auto-fluorescence imaging, fluorescence-lifetime imaging), some embodiments of the medical-imaging system 10 perform other modalities of imaging (e.g., near infrared spectroscopy (NIRS)) in addition to, or in alternative to, fluorescence imaging or OCT imaging.

During optical-scanning procedures, the medical-imaging system 10 may detect blood clearance based on fluorescence excitation light, for example based on excitation light for auto-fluorescence light or excitation light for near-infrared auto-fluorescence (NIRAF) light (e.g., laser-induced NIRAF light); generate a clearance indicator (e.g., a trigger, an interrupt, a message) that indicates that blood clearance has been achieved; and automatically begin a pullback procedure when blood clearance has been achieved. Additionally, the medical-imaging system 10 may synchronize the beginning of data storage with the beginning of the pullback procedure.

When performing OCT scanning of vessels that carry blood, the blood cells strongly scatter the OCT light. Consequently, blood clearance (also referred to as blood flushing) is performed to improve the OCT scanning of the vessel. Blood clearance uses contrast agents, saline, dextran or other liquids to clear (flush) the blood cells out of a portion of the vessel. When blood cells are cleared out of the portion of the vessel, the medical-imaging system 10 performs OCT scanning of the portion of the vessel during a pullback procedure. Blood clearance occurs before the pullback procedure starts and, because the OCT pullback speed is fast (~2 sec/~40:100 mm pullback), it is advantageous for the pullback procedure to start immediately when the blood is cleared in order to allow imaging of the entire targeted region of the sample (e.g., vessel). Moreover, because the dosage of the contrast agents need to be lower than a specific dosage level, a second blood clearance (e.g., a second blood clearance that is performed because a first pullback procedure was unsuccessful) might be harmful to the patient.

To automatically start recording OCT-detection data (and other data) during the pullback, the medical-imaging system 10 may implement a trigger that is based on OCT images. However, implementing a trigger that is based on computed OCT images requires significant computational power, and achieving high-speed real-time acquisition of OCT images without a delay is difficult.

Various embodiments of the medical-imaging system 10, as well as embodiments of the devices and methods that are described herein, detect the clearance state of blood and automatically trigger a pullback and data recording without user interaction and without using a trigger that is based on OCT images or that requires significant computational resources. Such embodiments help to image the targeted regions of a sample without unnecessary delays and with minimal contrast-agent use. Some embodiments also detect the end of a clearance state, end the pullback, and end data recording, thus limiting stored data to clinically relevant data, which minimizes storage requirements and processing time.

In FIG. 1, the optical-imaging device 201 includes a catheter (e.g., a sheath) that surrounds an optical probe. Some embodiments of the optical-imaging device 201 include one or more optical fibers (e.g., a single clad fiber, a double clad fiber (DCF)) with a polished ball lens at the tip thereof for side-view scanning. The distal optics of the optical-imaging device 201 may also include a DCF, a GRIN lens, or a refractive element (e.g., grating). The optical-imaging device 201 can perform optical-scanning procedures inside a lumen (e.g., vessel, bronchus, intestine, trachea, ear canal) or cavity (e.g., stomach, nasal cavity).

Figure 2A:
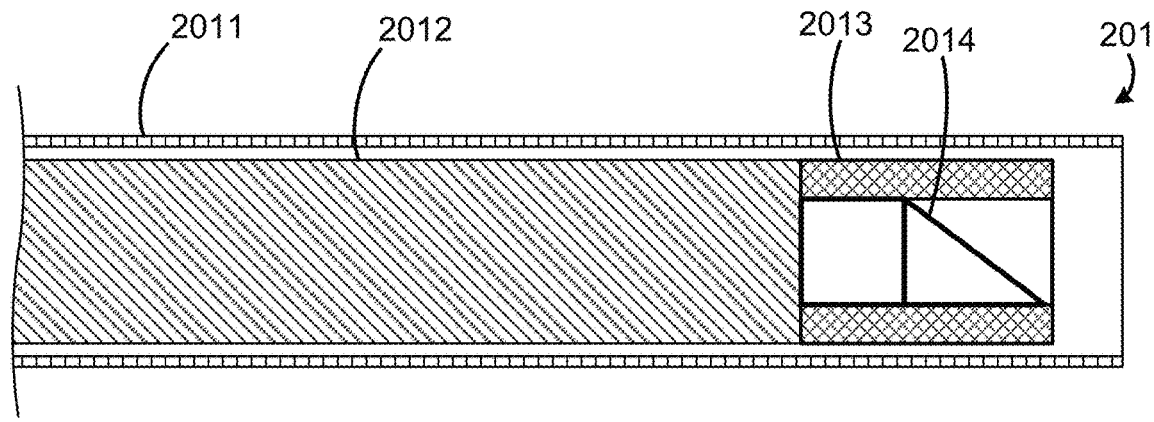
FIGS. 2A-2B illustrate an example embodiment of an optical-imaging device.
Figure 2B:
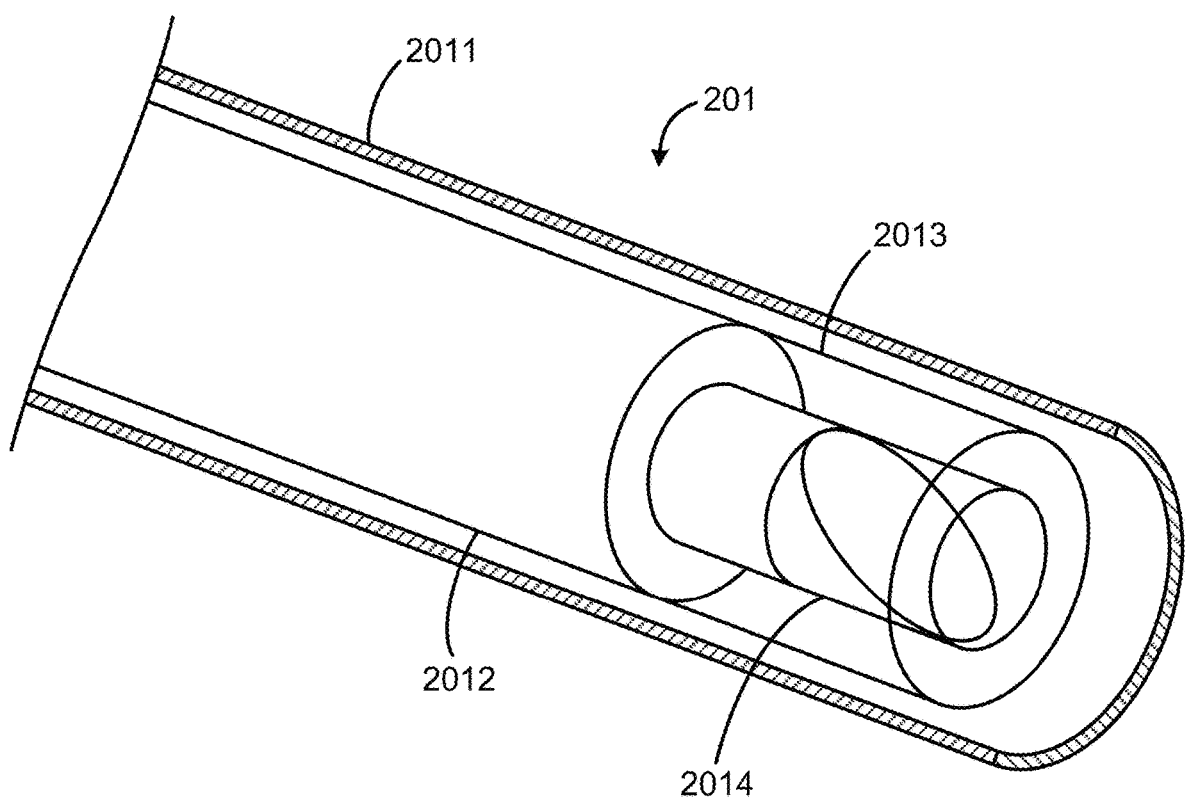

For example, FIGS. 2A-B illustrate an example embodiment of an optical-imaging device. FIG. 2A illustrates a partially cutaway side view of the optical-imaging device 201, and FIG. 2B illustrates a partially cutaway perspective view of the optical-imaging device 201.

The optical-imaging device 201 includes a catheter 2011 (e.g., a sheath), a coil 2012, a protector 2013, and an optical probe 2014. As shown in FIG. 1, the optical-imaging device 201 may be connected to the PIU 202, which can spin the coil 2012 during a pullback procedure. The coil 2012 delivers torque from its proximal end to its distal end. In some embodiments, the coil 2012 is fixed with, or to, the optical probe 2014 such that a distal tip of the optical probe 2014 also spins with the coil 2012, which provides the optical probe 2014 with a panoramic or multidirectional view. As a beam of light travels through the optical probe 2014, the optical probe 2014 can be rotated, thereby providing the optical probe 2014 with views of a surface of interest. Furthermore, the optical probe 2014 can simultaneously be translated longitudinally during the rotation, which results in a helical scanning pattern. This translation is most commonly performed by pulling the tip of the optical probe 2014 back towards the proximal end and is therefore referred to as a pullback procedure.

In some embodiments, the optical probe 2014 comprises an optical-fiber connector, an optical fiber, and a distal lens. The optical-fiber connector may be used to engage with the PIU 202, and the optical fiber may operate to deliver light to the distal lens. For example, a DCF may transmit and collect OCT light through the core, and the DCF may transmit excitation light and collect Raman and fluorescence that is reflected by the sample through the clad. The distal lens may shape the beam of light, direct illuminating light to the sample, and collect light that is reflected from the sample. The optical probe 2014 may also include a mirror at the distal end that deflects a beam of light outward.

Figure 3:
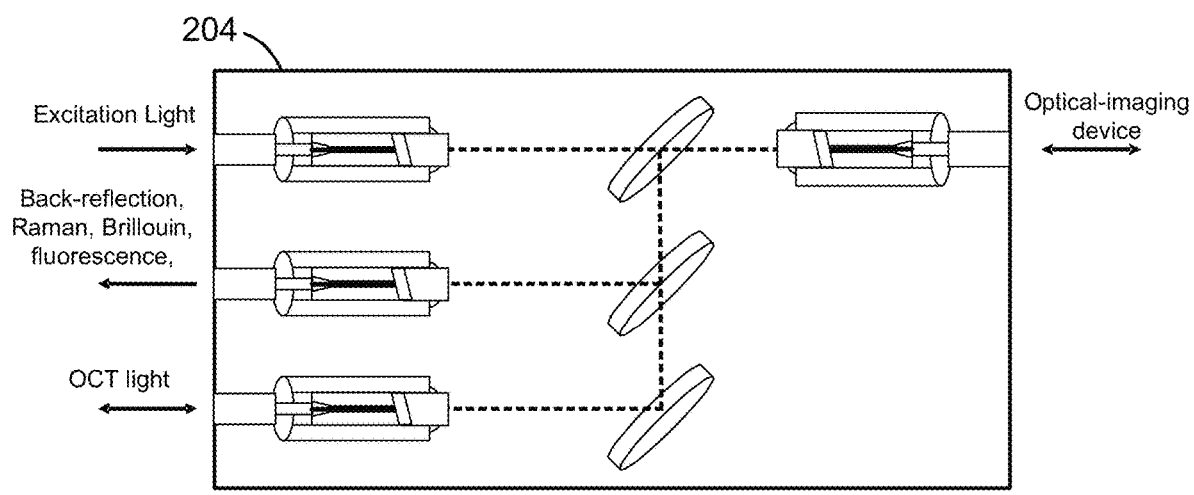
FIG. 3 illustrates an example embodiment of a beam combiner.

The PIU 202 includes a rotary junction 203 (e.g., a FORJ), a pullback unit 205, and a beam combiner 204. FIG. 3 illustrates an example embodiment of the beam combiner 204. The beam combiner 204 combines excitation light and OCT light, and the beam combiner 204 supplies the combined light to the one or more optical fibers of the optical-imaging device 201, which carry the combined light to the distal end of the optical-imaging device 201, where the OCT light and the excitation light illuminate a sample 400. Also, the beam combiner 204 separates OCT light that has been collected by the optical-imaging device 201 from back-reflected light, fluorescence light, Raman-scattered light, and Brillouin-scatted light that have been collected by the optical-imaging device 201.

During an optical-scanning procedure, the position of the optical probe 2014 in the optical-imaging device 201, as well as the rest of the optical-imaging device 201, can be adjusted or controlled by the pullback unit 205. Some embodiments of the pullback unit 205 include a rotational motor and a translation motorized stage. In some embodiments, the rotary junction 203 is located in the pullback unit 205. The rotary junction 203 allows the optical probe 2014 to rotate inside the optical-imaging device 201. During the rotation, which may be performed by the rotational motor, the optical probe 2014 (as well as the rest of the optical-imaging device 201) can be moved longitudinally (e.g., by a translation motorized stage) so that light (e.g., OCT light, fluorescence light) is collected in a helical scanning pattern. For example, the rotation and translation movements can helically scan the optical probe 2014 inside a lumen and can produce a series of adjacent helical A-scans of the lumen, which can then be used to create a helical two-dimensional (2D) tomogram. Also for example, moving the optical probe 2014 longitudinally within the lumen allows the collection of a series of B-scans, which can be combined to form a three-dimensional (3D) image of the lumen.

Return loss may reduce the measureable dynamic ranges of the signals that are transmitted by the optical-imaging device 201 and the PIU 202. Thus, in some embodiments of the optical-imaging device 201 and the PIU 202, at least some of the optical components have an optimized anti-reflection coating at the excitation wavelength. Also, a calibration value can be pre-determined and subtracted for PIU return loss and optical-imaging-device return loss. And some embodiments of the medical-imaging system 10 correct the return loss from the optics of the PIU 202 a priori and correct the return loss from the optics of the optical-imaging-device 201 only each time a new optical-imaging-device 201 is engaged to the PIU 202. Such embodiments may be particularly advantageous in cases in which there are several optical-imaging-device designs or variations.

The OCT-light source 300 generates OCT light (e.g., with a wavelength of approximately 1.3 μm), which is delivered to a splitter 301. The splitter 301 splits the OCT light into a reference arm 302 and a sample arm 306. The reference arm 302 includes the mirror 303 and the first circulator 304, and the sample arm 306 includes the optical-imaging-device 201 and the PIU 202. A reference beam of OCT light transmitted along the reference arm 302 is reflected from the mirror 303, is then transmitted to the first circulator 304, and is then transmitted to the OCT combiner 305. A sample beam of OCT light is transmitted through the second circulator 307, is transmitted along the sample arm 306 (through the one or more optical fibers of the optical-imaging device 201), is incident on a sample 400 (e.g., an organ, tissue), and is reflected or scattered by the sample 400. Some of the reflected or scattered OCT light is collected by the optical-imaging device 201, and the collected OCT light is transmitted through the optical-imaging device 201 (through the one or more optical fibers of the optical-imaging device 201), through the rotary junction 203, through the beam combiner 204 (which separates the OCT light from the other collected light), and through the second circulator 307 to an OCT combiner 305.

In the OCT combiner 305, the OCT light from the reference arm 302 and the collected OCT light reflected from the sample 400 are combined, thereby generating interference patterns. The combined light, which includes the interference patterns, is detected by the OCT detector 308 (e.g., a photodiode, a multi-array camera), which generates an OCT-detection signal that carries OCT-detection data based on the combined light. The OCT-detection signal is supplied to an OCT unit 110 of the imaging station 100. The OCT unit 110 obtains and processes the OCT-detection data.

Additionally, excitation light generated by an excitation-light source 310 is transmitted through the beam combiner 204 to the rotary junction 203, and then to the distal end of the optical-imaging device 201 to illuminate the sample 400. In some embodiments, the excitation light has one of the following wavelengths or wavelength ranges: approximately 0.633 μm, 0.633-0.90 μm, and 0.500-0.700 μm. The excitation light incident on the sample 400 causes the sample 400 to emit fluorescence light. In some embodiments, the fluorescence light generated by the sample 400 includes autofluorescence light, which is the endogenous fluorescence light that is generated without application of a dye or an agent. And the fluorescence light generated by the sample 400 may include fluorescence light generated by exogenous fluorescence dye or agent in the sample 400. Furthermore, some of the excitation light may be reflected from the sample back to the optical probe. Such reflected excitation light may be referred to herein as "back-reflected excitation light."

The optical-imaging device 201 collects fluorescence light (e.g., autofluorescence light), Raman-scattered light, Brillouin-scattered light, and back-reflected excitation light (as well as OCT light) that are emitted or reflected by the sample 400. The fluorescence light has wavelengths that are larger than the excitation light's wavelengths, and the signal of the back-reflected excitation light is several orders of magnitude larger than the signal of the fluorescence light.

The one or more optical fibers carry the collected light to the proximal end of the optical-imaging device 201.

After traveling through the beam combiner 204, the fluorescence light emitted from the sample 400, Raman-scattered light, Brillouin-scattered light, and back-reflected excitation light are supplied to a dichroic filter 311, which directs the fluorescence light to the fluorescence detector 315 (e.g., a photomultiplier tube (PMT)).

Also, this embodiment of the imaging subsystem 50 includes a line filter 314 (e.g., a laser line filer). The line filter 314 reduces signal washout from any remaining back-reflected excitation light that reaches the fluorescence detector 315. For example, the line filter 314 can be narrow with a high filtering capability for the NIRAF excitation wavelength (e.g., 635 nm), with only a couple of nanometers of bandwidth, or the bandwidth can be broader (e.g., up more than 2 nm and less than 20 nm or 40 nm) to reduce Raman signals from an optical fiber that can affect NIRAF signal-to-noise ratio.

Based on the received fluorescence light, the fluorescence detector 315 generates a fluorescence-detection signal that carries fluorescence-detection data that include detected values of the fluorescence light (detected fluorescence values). The detected fluorescence values may indicate the intensities of the detected fluorescence light. The fluorescence detector 315 provides the fluorescence-detection signal, which carries the fluorescence-detection data, to a fluorescence-processing unit 120 of the imaging station 100. The fluorescence-processing unit 120 obtains and processes the fluorescence-detection data. In some embodiments, the OCT-detection signal and the fluorescence-detection signal are supplied to the imaging station 100 concurrently or simultaneously.

Based on the detection data (e.g., OCT-detection data, fluorescence-detection data) that is obtained during an optical-scanning procedure, the imaging station 100 generates an OCT image, a fluorescence image, or a multi-modal image, such as an OCT-fluorescence image (e.g., a co-registered OCT-fluorescence image), and the imaging station 100 provides the image to a display device 500, which displays the image.

Also, the dichroic filter 311 directs the back-reflected excitation light to a reflectance detector 316. Based on the received back-reflected excitation light, the reflectance detector 316 generates a reflectance-detection signal that carries back-reflected-excitation-light-detection data that include detected values of the back-reflected excitation light, which may indicate the intensity of the back-reflected excitation light, and supplies the reflectance-detection signal to the blood-clearance monitor 130.

In some embodiments of the imaging subsystem 50, the dichroic filter 311 is replaced with an optical switch that controls which detector, of the fluorescence detector 315 and the reflectance detector 316, receives the signal that includes the fluorescence light and the back-reflected excitation from the PIU 202. In a pullback-ready mode, the switch directs the signal to the reflectance detector 316, and the switch then directs the signal to the fluorescence detector 315 in response to the generation of a clearance indicator, which indicates that blood clearance has been achieved. After the pullback procedure is finished, the switch directs the signal to the reflectance detector 316. Also, the switch can be controlled to switch to the fluorescence detector 315 (e.g., for calibration). Furthermore, some embodiments of the imaging subsystem 50 include a mirror that can be repositioned by an electric solenoid to direct the signal to either the reflectance detector 316 or the fluorescence detector 315.

The blood-clearance monitor 130 monitors the intensity of the back-reflected excitation light. When, based on the back-reflected excitation light, the blood-clearance monitor 130 detects that blood has been cleared, the blood-clearance monitor 130 generates a clearance indicator (e.g., a trigger), which indicates that blood clearance has been achieved, and provides the clearance indicator to the imaging station 100. The generation of the clearance indicator may initiate the performance of operations in the medical-imaging system 10. For example, some embodiments of the blood-clearance monitor 130 generate a trigger (e.g., a trigger signal) that triggers an event in the medical-imaging system 10. Also, the blood-clearance monitor 130 may send a signal (e.g., the clearance indicator) to the pullback unit 205 to cause the pullback unit 205 to begin a pullback procedure and may send a signal (e.g., the clearance indicator) to the excitation-light source 310 to cause the excitation-light source 310 to increase the intensity of the supplied excitation light.

When performing an optical-scanning procedure, the PIU 202 may start spinning the optical probe 2014 at a set rotation speed. Detecting blood clearance while the optical probe 2014 is spinning may minimize errors that are caused by catheter 2011 or optical probe 2014 eccentricity. For example, the catheter 2011 may be touching a wall of the lumen and, consequently, for a portion of the circumferential orientation, the excitation light only or mostly illuminates the wall of the lumen and not blood or contrast. Also, the medical-imaging system 10 may control the imaging subsystem 50 to supply the excitation light and, in some embodiments, the OCT light, to the distal end of the optical probe 2014. The excitation light may be supplied at an intensity that is set for blood-clearance monitoring. The blood-clearance monitor 130 can continuously or continually monitor the intensity of the back-reflected excitation light before pullback to determine whether to issue a clearance indicator (e.g., a trigger).

Once a clearance indicator has been issued, the medical-imaging system 10 can perform several operations simultaneously, nearly simultaneously, or explicitly delayed from each other. Examples of the operations include the following: activating the OCT-light source 300; activating the OCT detector 308; begin the recording of OCT-detection data in storage; sending a signal to make sure that the power of the excitation-light source 310 is set at an intensity for imaging; begin the recording of fluorescence-detection data in storage; sending a signal to a controller of the pullback unit 205 to enable a pullback procedure according to previously set pullback parameters; activating the fluorescence detector 315; and offsetting a data-acquisition-record-enable signal by 1-4 ms to account for any delay in linear pullback-motor acceleration in the pullback unit 205.

Furthermore, in some embodiments, the blood-clearance monitor 130 monitors the intensity of the back-reflected excitation light during pullback to determine whether to issue another indicator (e.g., issue a non-clearance indicator when blood clearance ends), which may instruct the medical-imaging system 10 to stop recording detection data (OCT-detection data, fluorescence-detection data), stop the pullback procedure, stop light emission, or decrease the intensity of emitted light.

Figure 4:
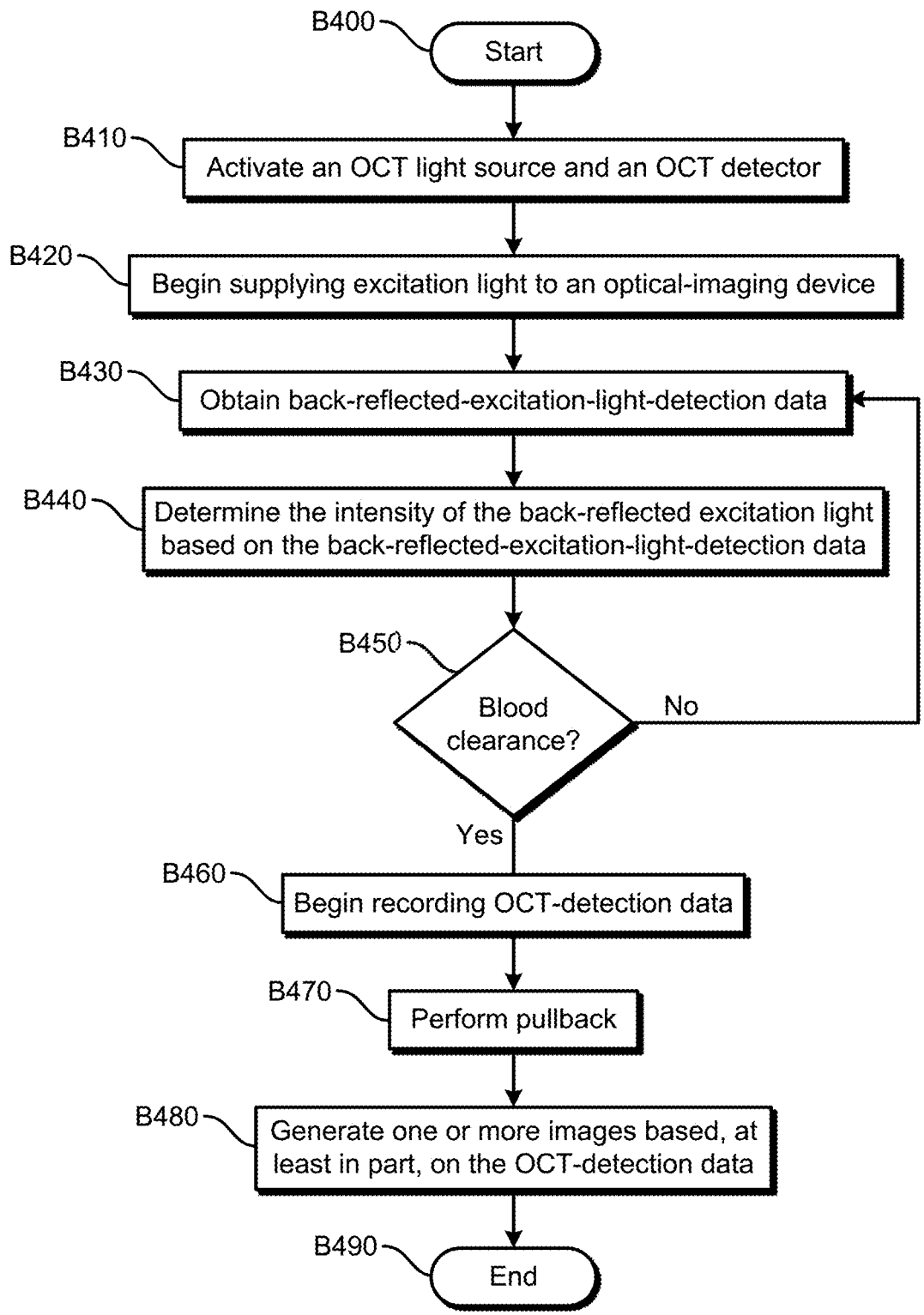
FIG. 4 illustrates an example embodiment of an operational flow for an optical-scanning procedure.

FIG. 4 illustrates an example embodiment of an operational flow for an optical-scanning procedure. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. Thus, other embodiments of the operational flows that are described herein may omit blocks, add blocks, change the order of the blocks, combine blocks, or divide blocks into more blocks.

In FIG. 4, the flow starts in block B400 and then moves to block B410, where a medical-imaging system activates an OCT-light source and an OCT detector. However, before block B460, the medical-imaging system may discard any OCT-detection data.

Next, in block B420, the medical-imaging system begins supplying excitation light to an optical-imaging device. For example, the medical-imaging system may activate an excitation-light source. Also, the light output of the excitation-light source may be a fraction of the normal light output for imaging. For example, the light output may be sufficient for the medical-imaging system to detect changes in back-reflected excitation light with a sufficient signal-to-noise ratio and without photo-bleaching the imaged tissue.

The flow then proceeds to block B430, where the medical-imaging system obtains back-reflected-excitation-light-detection data. For example, the optical-imaging device may collect back-reflected excitation light that was reflected by fluid in a vessel, by the vessel, or by other tissue and transmit the back-reflected excitation light to a reflectance detector, which generates back-reflected-excitation-light-detection data.

The flow then proceeds to block B440, where the medical-imaging system determines the intensity of the back-reflected excitation light based on the back-reflected-excitation-light-detection data.

Arterial, venous, and completely deoxygenated blood have distinct reflectance spectra (e.g., reflectance curves, where the y-axis is reflection percentage and the x-axis is wavelength). For example, arteries carry oxygenated blood, which reflects more light (e.g., OCT light, excitation light) than deoxygenated blood. The maximal reflectance for arterial blood is approximately 650 nm, which is close to the NIRAF excitation wavelength of approximately 635 nm. Factors that affect blood reflectance include hematocrit (HCT) percentage, which typically varies based on gender and health condition, but is considered in the normal range if it is between about 35% and 49%. However, the percentage can be higher, especially for patients with heart disease. Blood reflectance typically increases with increasing HCT percentage and starts to levels off at about 40%. For example, the variation in blood reflectance can be as high as two times between a 22% HCT percentage and a 45% HCT percentage. Thus, blood may be a good reflector, although the reflectance can vary from person to person and can vary from day to day according to the person's health and other factors, such as dehydration.

Furthermore, the reflectance of contrast media is extremely low. The reflectance change of blood to contrast media may be greater than a factor of ten even when accounting for all variations in starting reflectance of the different HCT percentages and oxygenation levels of blood. Consequently, reflectance in a vessel decreases as blood is displaced and replaced with contrast media. Additionally, different contrast media are able to more efficiently displace blood than others. For example, Visipaque is able to displace blood quicker and better than saline, and thus produces a reflectance change that is quicker and more pronounced than saline.

Thus, the intensity of the back-reflected excitation light decreases as blood is cleared and replaced with contrast media.

The flow then moves to block B450, where the medical-imaging system (e.g., a blood-clearance monitor, an imaging station) determines whether blood clearance has been achieved based on the intensity of the back-reflected excitation light. For example, the medical-imaging system may determine that blood clearance has been achieved if the intensity of the back-reflected excitation light falls below a threshold, if the intensity of the back-reflected excitation light falls below a threshold and remains below the threshold for a set period of time, or if a rate of change of the intensity of the back-reflected excitation light rises above (or falls below) a threshold.

Figure 5A:
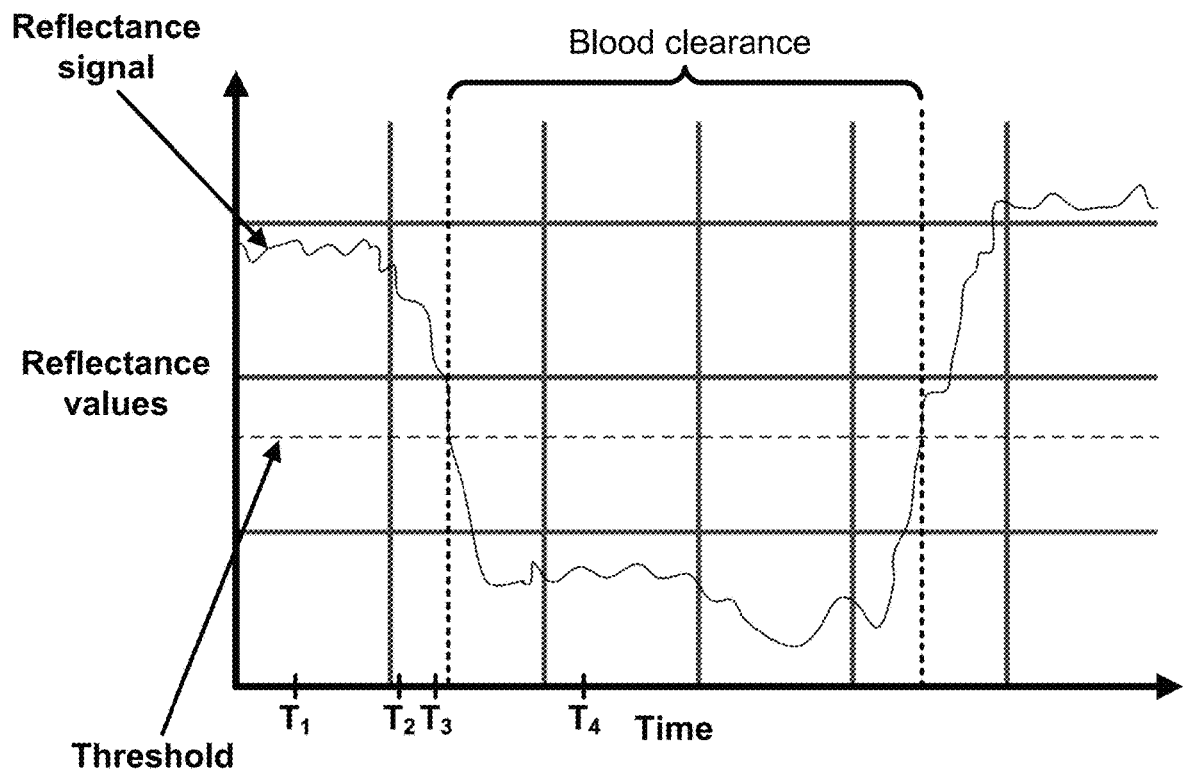
FIG. 5A is a graph that illustrates examples of reflectance values.

If the medical-imaging system determines that blood clearance has not been achieved (B450=No), then the flow returns to block B430. Thus, in blocks B430-6450, the medical-imaging system may continuously or continually obtain back-reflected-excitation-light-detection data, determine the intensity of the back-reflected excitation light based on the back-reflected-excitation-light-detection data, and determine whether blood clearance has been achieved based on the intensity of the back-reflected excitation light. For example, FIG. 5A is a graph that illustrates the intensity of the back-reflected excitation light over a period of time. In FIG. 5A, the intensity of the back-reflected excitation light varies over time and, at the time when the intensity falls below a threshold, the medical-imaging system determines that blood clearance has been achieved. Also, at the time when the intensity rises above the threshold, some embodiments of the medical-imaging system determine that blood clearance has ended.

Figure 5B:
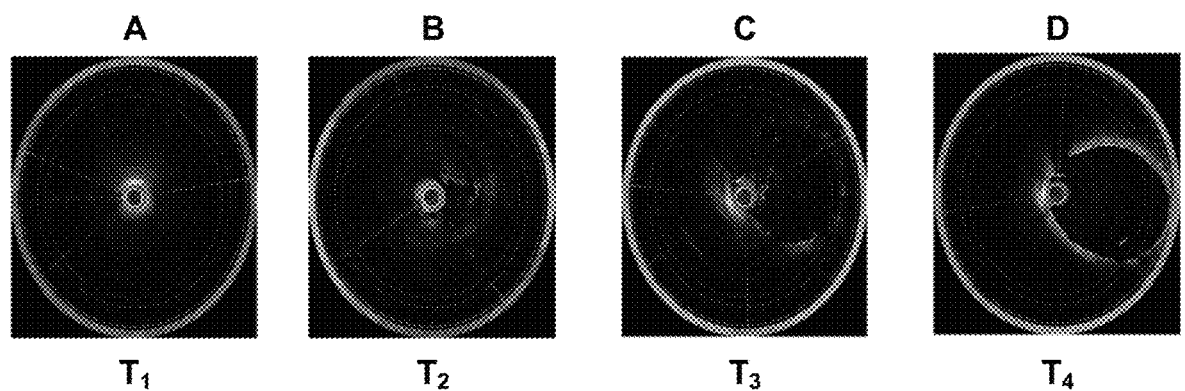
FIG. 5B illustrates images that were generated based on OCT-detection data.

If the medical-imaging system determines that blood clearance has been achieved (B450=Yes), then the flow advances to block B460. In block B460, the medical-imaging system begins recording OCT-detection data in storage. Next, in block B470, the medical-imaging system performs a pullback. The flow then moves to block B480, where the medical-imaging system generates one or more images based, least in part, on the OCT-detection data that are obtained during blood clearance. For example, FIG. 5B illustrates images that were generated based on OCT-detection data. The four images A-D were generated based on OCT-detection data that were obtained at the following times in FIG. 5A: $T_1$, $T_2$, $T_3$, and $T_4$. Images A-C are included to illustrate images that were generated based on OCT-detection data that were not obtained during blood clearance, but some embodiments of the medical-imaging system 10 do not generate these images. In image A, the lumen is not visible because the blood blocks the OCT light. In image B, portions of the lumen a barely visible, but most of the lumen is still obscured. In image C, more of the lumen is visible, although parts of the lumen are still obscured. However, in image D, which was generated based on OCT-detection data that were obtained during blood clearance (e.g., in blocks B460-6470 in FIG. 4), all (or nearly all) of the lumen is visible.

Finally, the flow ends in block B490.

Figure 6:
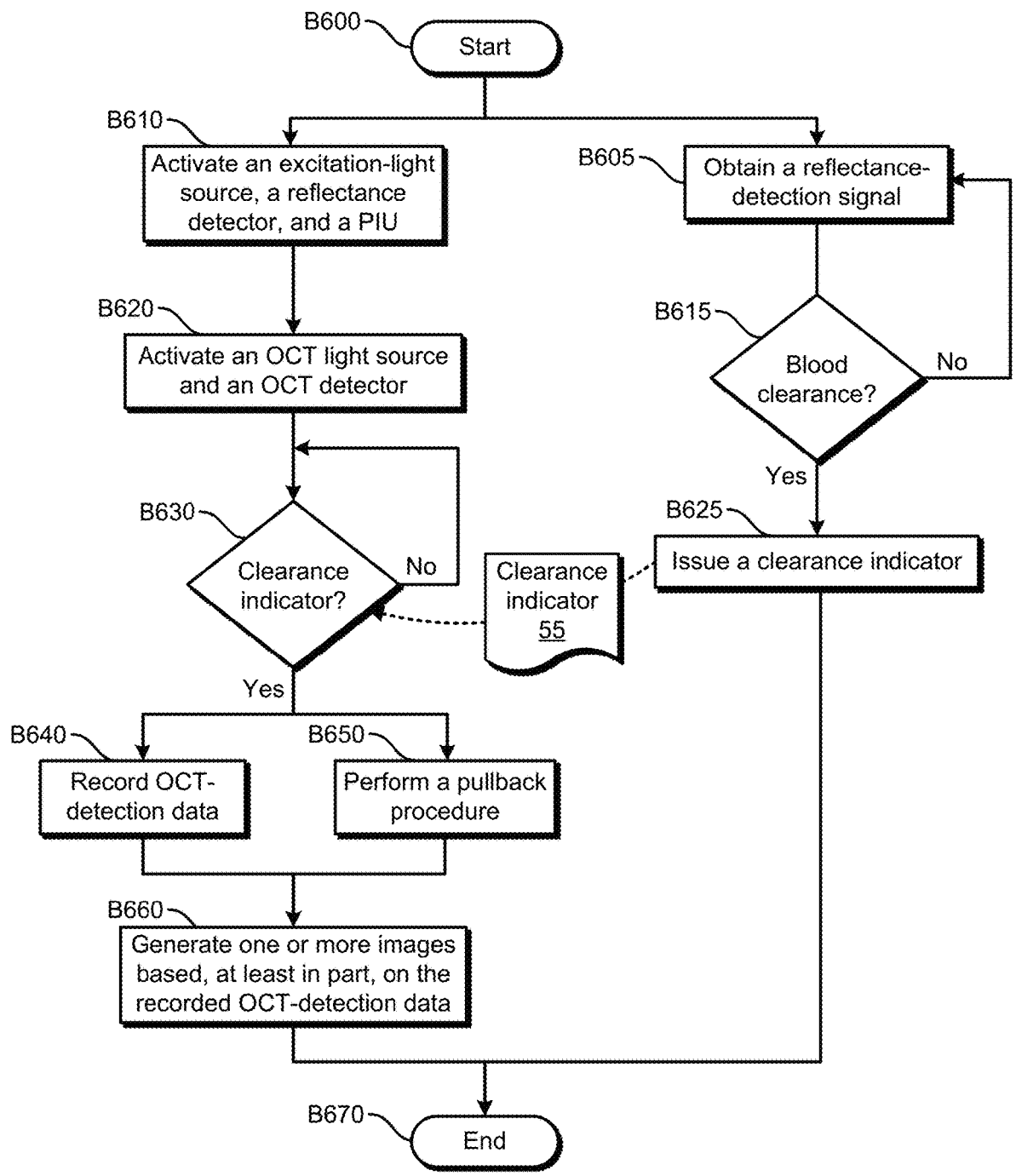
FIG. 6 illustrates an example embodiment of an operational flow for an optical-scanning procedure.

FIG. 6 illustrates an example embodiment of an operational flow for an optical-scanning procedure. The flow begins in block B600 and then splits into a first flow and a second flow.

Although, in this example embodiment, the operations in the first flow are performed by an imaging station, in some embodiments the operations in the first flow are performed by two or more imaging stations or by one or more other specially-configured computing devices.

Additionally, although the operations in the second flow in this example embodiment are performed by a blood-clearance monitor, in some embodiments the operations in the second flow are performed by two or more blood-clearance monitors or by one or more specially-configured computing devices. Also, one or more imaging stations may perform at least some of the operations in the second flow.

The first flow moves to block B610, where an imaging station instructs an imaging subsystem to activate an excitation-light source, a reflectance detector, and a PIU. In response to being activated, the PIU causes an optical probe, in an optical-imaging device, to spin. Next, in block B620, the imaging station instructs the imaging subsystem to activate an OCT-light source and an OCT detector. The first flow then proceeds to block B630, where the imaging station determines if a clearance indicator 55 has been issued. For example, some embodiments of the imaging station determine whether a blood-clearance-begin event has been triggered. If the imaging station determines that a clearance indicator 55 has not been issued (e.g., the blood-clearance-begin event has not been triggered) (B630=No), then the first flow returns to block B630, and the imaging station continues to wait for the clearance indicator 55. If the imaging station determines that the clearance indicator 55 has been issued (e.g., the blood-clearance-begin event has been triggered) (B630=Yes), then the first flow proceeds to block B640 and block B650.

In block B640, the imaging station records OCT-detection data in storage. The imaging station may discard OCT-detection data that are obtained before block B640. And, in some embodiments, the imaging station deactivates the excitation-light source or, alternatively, increases the output intensity of the excitation-light source.

In block B650, the imaging station instructs a pullback unit to perform a pullback procedure.

Also, in some embodiments, blocks B640 and B650 are performed simultaneously or nearly simultaneously. Also, in some embodiments, block B650 is started before block B640 is started. And block B640 may be started after waiting for a set delay time (e.g., 1-4 ms) after the beginning of block B650, which may compensate for any delay in linear pullback-motor acceleration in the pullback unit.

Next, in block B660, the imaging station generates one or more images based, at least in part, on the recorded OCT-detection data. The first flow then ends in block B670.

From block B600, the second flow proceeds to block B605. In block B605, a blood-clearance monitor obtains a reflectance-detection signal, which includes back-reflected-excitation-light-detection data.

The second flow then advances to block B615, where the blood-clearance monitor determines, based on the reflectance-detection signal, whether blood clearance has been achieved. For example, the blood-clearance monitor may determine that blood clearance has been achieved if one or more conditions are satisfied. Examples of the condition include the following: whether the strength of the reflectance-detection signal (e.g., the voltage of the signal, the current of the signal, the power of the signal, the amplitude of the signal) falls below a threshold, whether the strength of the reflectance-detection signal falls below a threshold and remains below the threshold for a set period of time, whether the intensity of the back-reflected excitation light falls below a threshold, whether the intensity of the back-reflected excitation light falls below a threshold and remains below the threshold for a set period of time, whether a rate of change of the intensity of the back-reflected excitation light rises above (or falls below) a threshold, and whether a rate of change of the intensity of the back-reflected excitation light rises above (or falls below) a threshold and remains below the threshold for a set period of time.

If the blood-clearance monitor determines that blood clearance has not been achieved (B615=No), then the second flow returns to block B605. If the blood-clearance monitor determines that blood clearance has been achieved (B615=Yes), then the second flow moves to block B625.

In block B625, the blood-clearance monitor issues a clearance indicator 55, for example by triggering an event (e.g., a blood-clearance-begin event). The second flow then ends in block B670.

Figure 7:
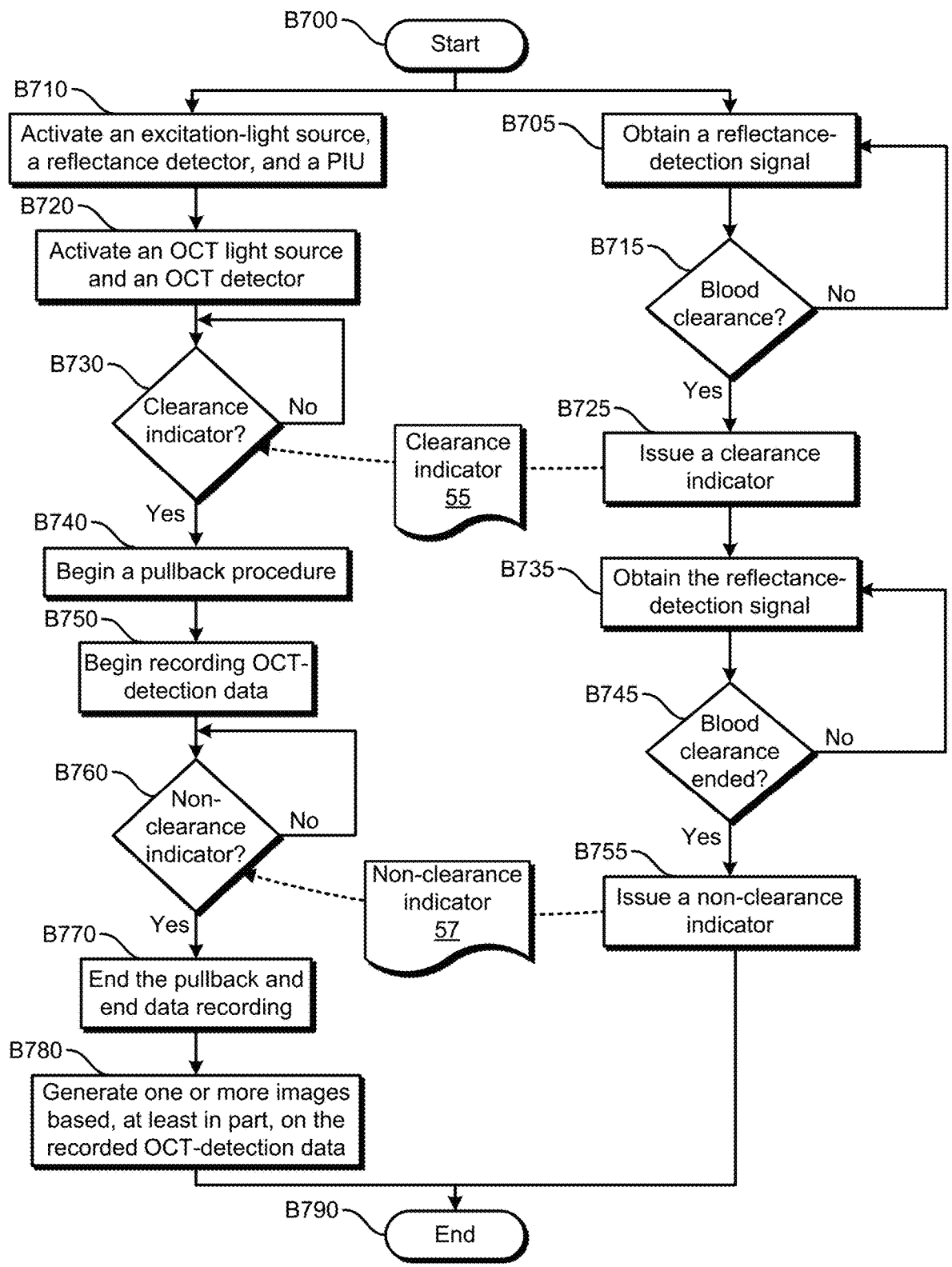
FIG. 7 illustrates an example embodiment of an operational flow for an optical-scanning procedure.

FIG. 7 illustrates an example embodiment of an operational flow for an optical-scanning procedure. The flow begins in block B700 and then splits into a first flow and a second flow.

Although, in this example embodiment, the operations in the first flow are performed by an imaging station, in some embodiments the operations in the first flow are performed by two or more imaging stations or by one or more other specially-configured computing devices.

Additionally, although the operations in the second flow in this example embodiment are performed by a blood-clearance monitor, in some embodiments the operations in the second flow are performed by two or more blood-clearance monitors or by one or more other specially-configured computing devices. Also, one or more imaging stations may perform the operations in the second flow.

The first flow moves to block B710, where an imaging station instructs an imaging subsystem to activate an excitation-light source, a reflectance detector, and a PIU. In response to being activated, the PIU causes an optical probe (in an optical-imaging device) to spin. Next, in block B720, the imaging station instructs the imaging subsystem to activate an OCT-light source and an OCT detector. The first flow then proceeds to block B730, where the imaging station determines if a clearance indicator 55 has been issued. For example, the imaging station may determine whether a first event (e.g., a blood-clearance-begin event) has been triggered. If the imaging station determines that the clearance indicator 55 has not been issued (B730=No), then the first flow returns to block B730, and the imaging station continues to wait for the clearance indicator 55 to be issued. If the imaging station determines that the clearance indicator 55 has been issued (B730=Yes), then the first flow proceeds to block B740.

In block B740, the imaging station instructs a pullback unit to begin a pullback procedure. Then, in block B750, the imaging station begins recording OCT-detection data in storage. The imaging station may discard OCT-detection data that are obtained before block B740. And, in some embodiments, the imaging station deactivates the excitation-light source or changes the intensity of the excitation-light source. Also, in some embodiments, blocks B740 and B750 are performed simultaneously or nearly simultaneously. And block B750 may be started after a set period of time has passed from the beginning of block B740.

The first flow then moves to block B760, where the imaging station determines whether a non-clearance indicator 57 has been issued. For example, the imaging station may determine whether a blood-clearance-end event has been triggered. If the imaging station determines that the non-clearance indicator 57 has not been issued (B760=No) (e.g., determines that the blood-clearance-end event has not been triggered), then the first flow returns to block B760, the pullback unit continues the pullback, and the recording of OCT-detection data continues. If the imaging station determines that the non-clearance indicator 57 has been issued (B760=Yes) (e.g., determines that the blood-clearance-end event has been triggered), then the first flow proceeds to block B770.

In block B770, the imaging station instructs the pullback unit to end the pullback procedure, and the imaging station ends the recording of the OCT-detection data. Next, in block B780, the imaging station generates one or more images based, at least in part, on the recorded OCT-detection data. The first flow then ends in block B790.

From block B700, the second flow proceeds to block B705. In block B705, a blood-clearance monitor obtains a reflectance-detection signal, which carries back-reflected-excitation-light-detection data. The second flow then moves to block B715, where the blood-clearance monitor determines, based on the reflectance-detection signal, whether blood clearance has been achieved. If the blood-clearance monitor determines that blood clearance has not been achieved (B715=No), then the second flow returns to block B705. If the blood-clearance monitor determines that blood clearance has been achieved (B715=Yes), then the second flow moves to block B725.

In block B725, the blood-clearance monitor issues a clearance indicator 55. For example, the blood-clearance monitor may trigger a first event (e.g., a blood-clearance-begin event).

The second flow then moves to block B735, where the blood-clearance monitor continues to obtain the reflectance-detection signal. Next, in block B745, the blood-clearance monitor determines, based on the reflectance-detection signal, whether blood clearance has ended. If the blood-clearance monitor determines that blood clearance has not ended (B745=No), then the second flow returns to block B735. If the blood-clearance monitor determines that blood clearance has ended (B745=Yes), then the second flow moves to block B755.

In block B755, the blood-clearance monitor issues a non-clearance indicator 57. For example, in some embodiments, the blood-clearance monitor triggers a second event (e.g., a blood-clearance-end event). The second flow then ends in block B790.

Figure 8:
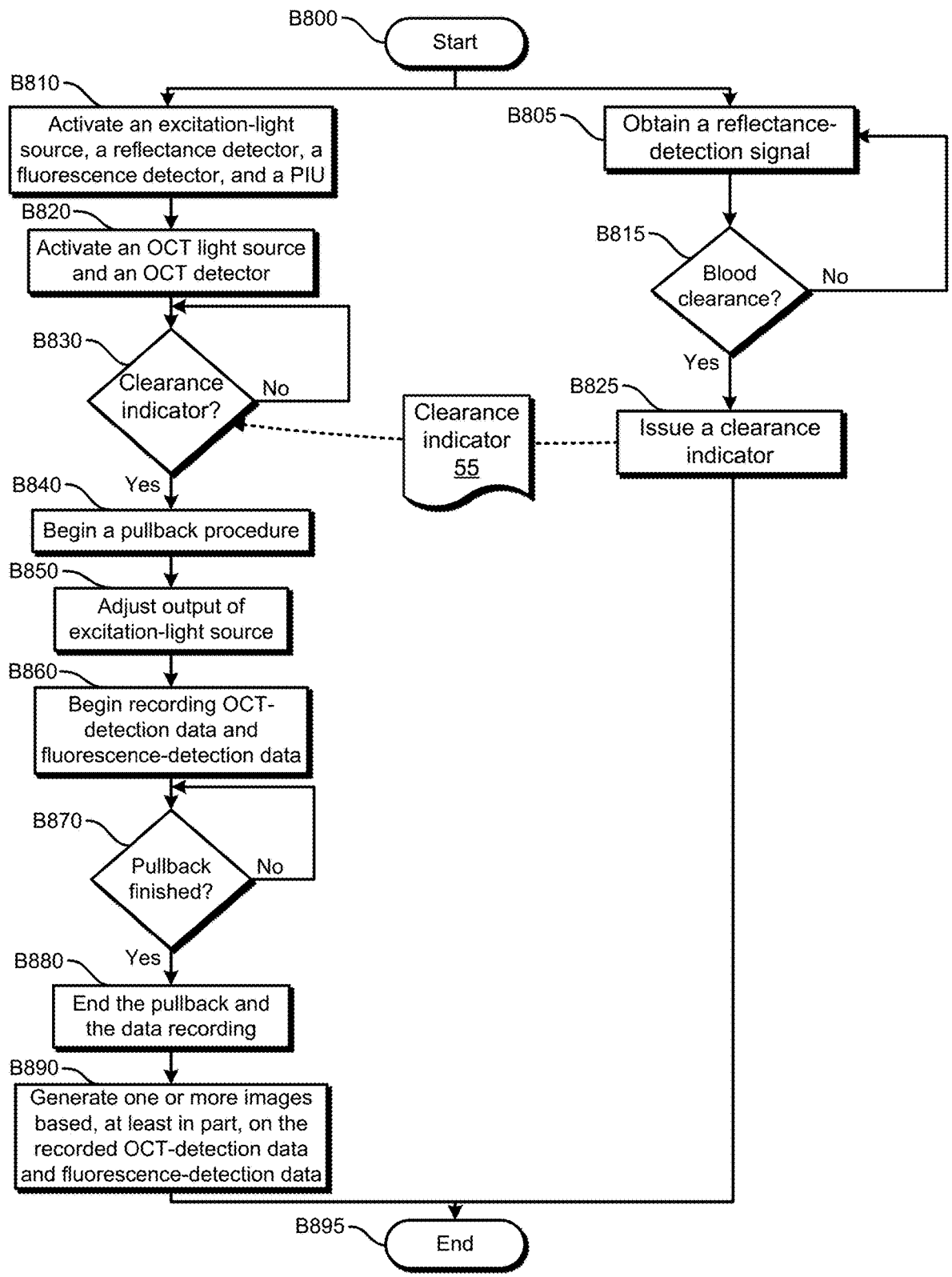
FIG. 8 illustrates an example embodiment of an operational flow for an optical-scanning procedure.

FIG. 8 illustrates an example embodiment of an operational flow for an optical-scanning procedure. The flow begins in block B800 and then splits into a first flow and a second flow.

Although, in this example embodiment, the operations in the first flow are performed by an imaging station, in some embodiments the operations in the first flow are performed by two or more imaging stations or by one or more other specially-configured computing devices.

Additionally, although the operations in the second flow in this example embodiment are performed by a blood-clearance monitor, in some embodiments the operations in the second flow are performed by two or more blood-clearance monitors or by one or more other specially-configured computing devices. Also, one or more imaging stations may perform at least some of the operations in the second flow.

The first flow moves to block B810, where an imaging station instructs an imaging subsystem to activate an excitation-light source, a reflectance detector, a fluorescence detector, and a PIU. In response to being activated, the PIU may cause an optical probe, in an optical-imaging device, to spin. Next, in block B820, the imaging station instructs the imaging subsystem to activate an OCT-light source and an OCT detector. The first flow then proceeds to block B830, where the imaging station determines if a clearance indicator 55 has been issued. If the imaging station determines that the clearance indicator 55 has not been issued (B830=No), then the first flow returns to block B830, and the imaging station continues to wait for the clearance indicator 55 to be issued. If the imaging station determines that the clearance indicator 55 has been issued (B830=Yes), then the first flow proceeds to block B840.

In block B840, the imaging station instructs a pullback unit to begin a pullback procedure. Next, in block B850, the imaging station instructs the excitation-light source to adjust its output. For example, the output power of the excitation-light source may be lower before the detection of blood clearance than during fluorescence imaging. The lower output power may reduce or prevent photobleaching. Thus, in some embodiments, the imaging station instructs the excitation-light source to increase the intensity of the output excitation light. Furthermore, in embodiments that include an imaging subsystem that includes an optical switch or a mirror that can be changed between one setting, in which the optical switch or mirror directs fluorescence light and back-reflected excitation light along a path to a reflectance detector, and another setting, in which the optical switch or mirror directs fluorescence light and back-reflected excitation light along a path to a fluorescence detector, the imaging station may control the optical switch or mirror to change to the position that directs fluorescence light and back-reflected excitation light along the path to the fluorescence detector (this path may also include a filter that removes the back-reflected excitation light).

In block B860, the imaging station begins recording OCT-detection data and fluorescence-detection data in storage. The imaging station may discard OCT-detection data and fluorescence-detection data that are obtained before block B860. Also, in some embodiments, the operations in blocks B840-6860 are performed simultaneously, nearly simultaneously, or according to a predetermined schedule (e.g., with predetermined delays between two or more of the operations).

The first flow then advances to block B870, where the imaging station determines whether the pullback procedure is finished. For example, the imaging station may determine that the pullback procedure is finished after a certain period of time has elapsed, after the optical probe has traveled a set distance, after a particular amount of detection data (OCT-detection data or fluorescence-detection data) has been obtained, or in response to a user input. If the imaging station determines that the pullback procedure is not finished (B870=No), then the first flow returns to block B870 and the pullback continues. If the imaging station determines that the pullback procedure is finished (B870=Yes), then the first flow moves to block B880, where the imaging station instructs the pullback unit to end the pullback. Also, the imaging station may end the recording of the OCT-detection data and the fluorescence-detection data. And the imaging station may instruct the imaging subsystem to deactivate one or more of the following: the excitation-light source, the reflectance detector, the fluorescence detector, the PIU, the OCT-light source, and the OCT detector.

Next, in block B890, the imaging station generates one or more images based, at least in part, on the recorded OCT-detection data and on the recorded fluorescence-detection data. The first flow then ends in block B895.

From block B800, the second flow proceeds to block B805. In block B805, a blood-clearance monitor obtains a reflectance-detection signal. The second flow then moves to block B815, where the blood-clearance monitor determines, based on the reflectance-detection signal, whether blood clearance has been achieved. If the blood-clearance monitor determines that blood clearance has not been achieved (B815=No), then the second flow returns to block B805. If the blood-clearance monitor determines that blood clearance has been achieved (B815=Yes), then the second flow moves to block B825.

In block B825, the blood-clearance monitor issues a clearance indicator 55. The second flow then ends in block B895.

Figure 9:
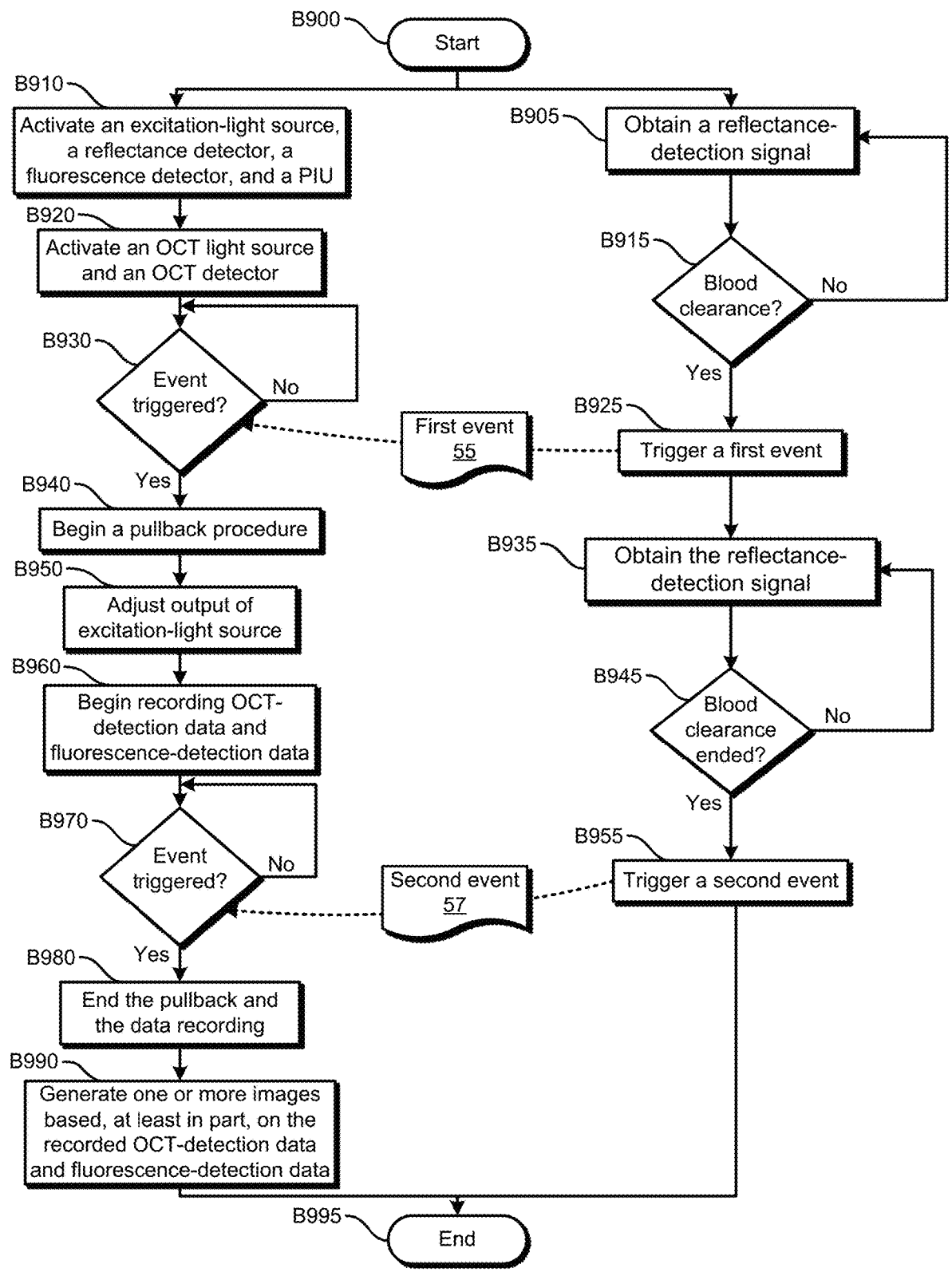
FIG. 9 illustrates an example embodiment of an operational flow for an optical-scanning procedure.

FIG. 9 illustrates an example embodiment of an operational flow for an optical-scanning procedure. The flow begins in block B900 and then splits into a first flow and a second flow.

Although, in this example embodiment, the operations in the first flow are performed by an imaging station, in some embodiments the operations in the first flow are performed by two or more imaging stations or by one or more other specially-configured computing devices. Additionally, although the operations in the second flow in this example embodiment are performed by a blood-clearance monitor, in some embodiments the operations in the second flow are performed by two or more blood-clearance monitors or by one or more other specially-configured computing devices. Also, one or more imaging stations may perform at least some of the operations in the second flow.

The first flow moves to block B910, where an imaging station instructs an imaging subsystem to activate an excitation-light source, a reflectance detector, a fluorescence detector, and a PIU. In response to being activated, the PIU may cause an optical probe, in an optical-imaging device, to spin. Next, in block B920, the imaging station instructs the imaging subsystem to activate an OCT-light source and an OCT detector. The first flow then proceeds to block B930, where the imaging station determines if a first event 55 (e.g., a blood-clearance-begin event) has been triggered. The first event 55 is an example of a clearance indicator. If the imaging station determines that the first event 55 has not been triggered (B930=No), then the first flow returns to block B930, and the imaging station continues to wait for the first event 55. If the imaging station determines that the first event 55 has been triggered (B930=Yes), then the first flow proceeds to block B940.

In block B940, the imaging station instructs a pullback unit to begin a pullback procedure.

Then, in block B950, the imaging station instructs the excitation-light source to adjust its output (e.g., to increase the intensity of its output excitation light). Furthermore, in embodiments that include an imaging subsystem that includes an optical switch or a mirror that can be changed between one setting, in which the optical switch or mirror directs fluorescence light and back-reflected excitation light along a path to a reflectance detector, and another setting, in which the optical switch or mirror directs fluorescence light and back-reflected excitation light along a path to a fluorescence detector, the imaging station may control the optical switch or mirror to change to the position that directs fluorescence light and back-reflected excitation light along the path to the fluorescence detector (this path may also include a filter that removes the back-reflected excitation light).

In block B960, the imaging station begins recording OCT-detection data and fluorescence-detection data in storage. The imaging station may discard OCT-detection data or fluorescence-detection data that are obtained before block B960. Also, in some embodiments, blocks B940-6960 are performed simultaneously or nearly simultaneously.

The first flow then advances to block B970, where the imaging station determines whether a second event 57 (e.g., a blood-clearance-end event) has been triggered. The second event 57 is an example of a non-clearance indicator. If the imaging station determines that the second event has not been triggered (B970=No), then the first flow returns to block B970 and the pullback procedure continues. If the imaging station determines that the second event has been triggered (B970=Yes), then the first flow moves to block B980. In block B980, the imaging station instructs the pullback unit to end the pullback. Also, the imaging station may end the recording of the OCT-detection data and the fluorescence-detection data. And the imaging station may instruct the imaging subsystem to deactivate one or more of the excitation-light source, the reflectance detector, the fluorescence detector, the PIU, the OCT-light source, and the OCT detector.

Next, in block B990, the imaging station generates one or more images based, at least in part, on the recorded OCT-detection data and on the recorded fluorescence-detection data. The first flow then ends in block B995.

From block B900, the second flow proceeds to block B905. In block B905, a blood-clearance monitor obtains a reflectance-detection signal. The second flow then moves to block B915, where the blood-clearance monitor determines, based on the reflectance-detection signal, whether blood clearance has been achieved. If the blood-clearance monitor determines that blood clearance has not been achieved (B915=No), then the second flow returns to block B905. If the blood-clearance monitor determines that blood clearance has been achieved (B915=Yes), then the second flow moves to block B925.

In block B925, the blood-clearance monitor triggers a first event 55 (e.g., a blood-clearance-begin event). The second flow then moves to block B935, where the blood-clearance monitor continues to obtain the reflectance-detection signal. And, in block B945, the blood-clearance monitor determines, based on the reflectance-detection signal, whether blood clearance has ended. If the blood-clearance monitor determines that blood clearance has not ended (B945=No), then the second flow returns to block B935. If the blood-clearance monitor determines that blood clearance has ended (B945=Yes), then the second flow advances to block B955. In block B955, the blood-clearance monitor triggers the second event 57 (e.g., a blood-clearance-end event). The second flow then ends in block B995.

Figure 10:
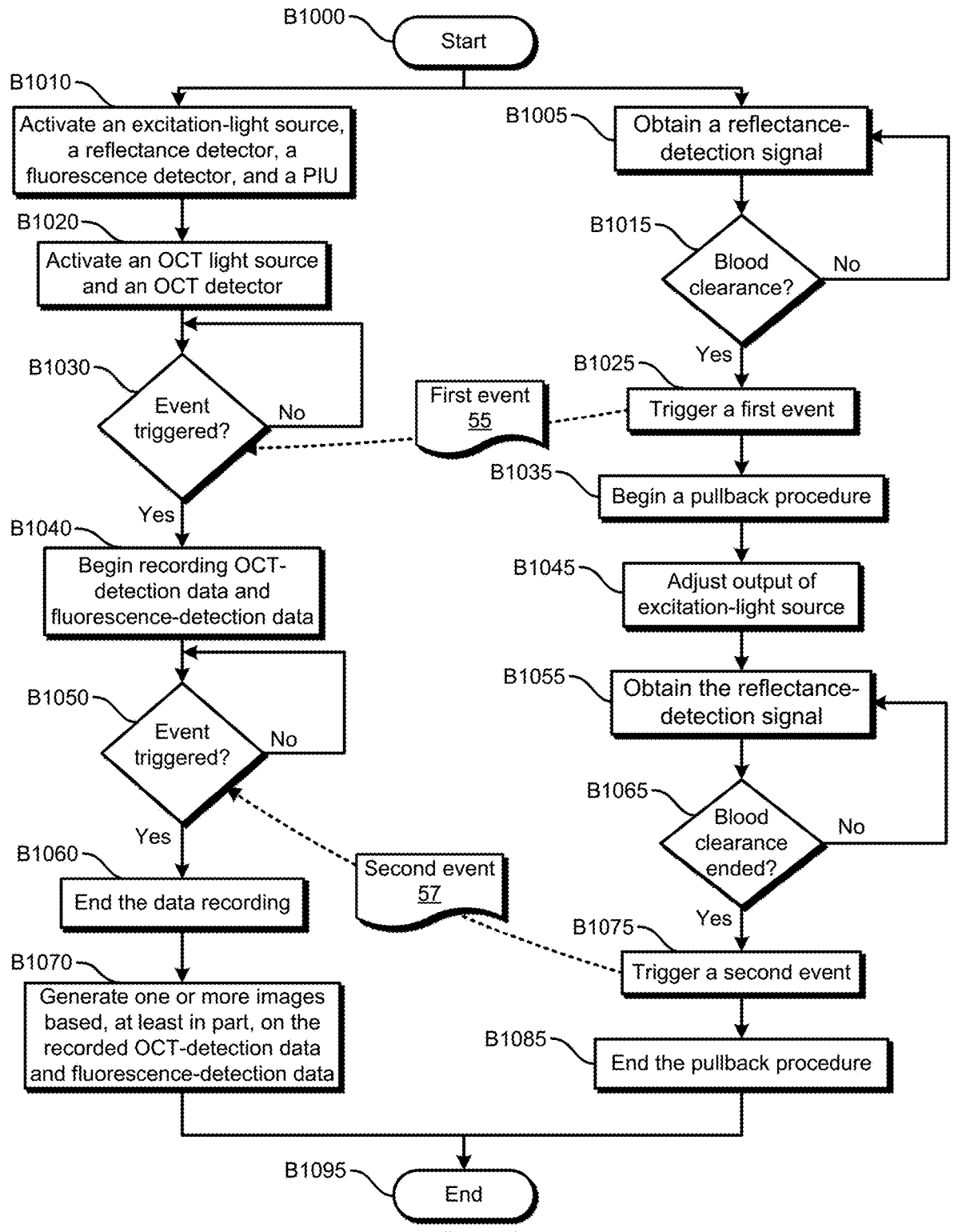
FIG. 10 illustrates an example embodiment of an operational flow for an optical-scanning procedure.

FIG. 10 illustrates an example embodiment of an operational flow for an optical-scanning procedure. The flow begins in block B1000 and then splits into a first flow and a second flow.

Although, in this example embodiment, the operations in the first flow are performed by an imaging station, in some embodiments the operations in the first flow are performed by two or more imaging stations or by one or more other specially-configured computing devices. Additionally, although the operations in the second flow in this example embodiment are performed by a blood-clearance monitor, in some embodiments the operations in the second flow are performed by two or more blood-clearance monitors or by one or more other specially-configured computing devices. Also, one or more imaging stations may perform at least some of the operations in the second flow.

The first flow moves to block B1010, where an imaging station instructs an imaging subsystem to activate an excitation-light source, a reflectance detector, a fluorescence detector, and a PIU. In response to being activated, the PIU may cause an optical probe, in an optical-imaging device, to spin. Next, in block B1020, the imaging station instructs the imaging subsystem to activate an OCT-light source and an OCT detector. The first flow then proceeds to block B1030, where the imaging station determines if a first event 55 (e.g., a blood-clearance-begin event) has been triggered. The first event 55 is an example of a clearance indicator. If the imaging station determines that the first event 55 has not been triggered (B1030=No), then the first flow returns to block B1030, and the imaging station continues to wait for the first event 55. If the imaging station determines that the first event 55 has been triggered (B1030=Yes), then the first flow proceeds to block B1040.

In block B1040, the imaging station begins recording OCT-detection data (and, in some embodiments, fluorescence-detection data) in storage. The imaging station may discard OCT-detection data or fluorescence-detection data that are obtained before block B1040.

The first flow then advances to block B1050, where the imaging station determines whether a second event 57 (e.g., a blood-clearance-end event) has been triggered. The second event 57 is an example of a non-clearance indicator. If the imaging station determines that the second event has not been triggered (B1050=No), then the first flow returns to block B1050 and the pullback procedure continues. If the imaging station determines that the second event has been triggered (B1050=Yes), then the first flow moves to block B1060. In block B1060, the imaging station ends the recording of the OCT-detection data and the fluorescence-detection data. And the imaging station may instruct the imaging subsystem to deactivate one or more of the following: the excitation-light source, the reflectance detector, the fluorescence detector, the PIU, the OCT-light source, and the OCT detector.

Next, in block B1070, the imaging station generates one or more images based, at least in part, on the recorded OCT-detection data and, in some embodiments, on the recorded fluorescence-detection data. The first flow then ends in block B1095.

From block B1000, the second flow proceeds to block B1005. In block B1005, a blood-clearance monitor obtains a reflectance-detection signal. The second flow then moves to block B1015, where the blood-clearance monitor determines, based on the reflectance-detection signal, whether blood clearance has been achieved. If the blood-clearance monitor determines that blood clearance has not been achieved (B1015=No), then the second flow returns to block B1005. If the blood-clearance monitor determines that blood clearance has been achieved (B1015=Yes), then the second flow moves to block B1025.

In block B1025, the blood-clearance monitor triggers a first event 55 (e.g., a blood-clearance-begin event). Then, in block B1035, the blood-clearance monitor instructs the PIU to being a pullback procedure. For example, the blood-clearance monitor may send a signal to the PIU that causes the PIU to begin the pullback procedure. The second flow then proceeds to block B1045, where the blood-clearance monitor instructs the excitation-light source to adjust (e.g., increase the intensity of) its output excitation light. Blocks B1035 and B1045 may be performed simultaneously, nearly simultaneously, or according to a predetermined timing schedule.

The second flow then moves to block B1055, where the blood-clearance monitor continues to obtain the reflectance-detection signal. And, in block B1065, the blood-clearance monitor determines, based on the reflectance-detection signal, whether blood clearance has ended. If the blood-clearance monitor determines that blood clearance has not ended (B1065=No), then the second flow returns to block B1055. If the blood-clearance monitor determines that blood clearance has ended (B1065=Yes), then the second flow advances to block B1075. In block B1075, the blood-clearance monitor triggers the second event 57 (e.g., a blood-clearance-end event). And, in block B1085, the blood-clearance monitor instructs the PIU to end the pullback procedure. The second flow then ends in block B1095.

Figure 11:
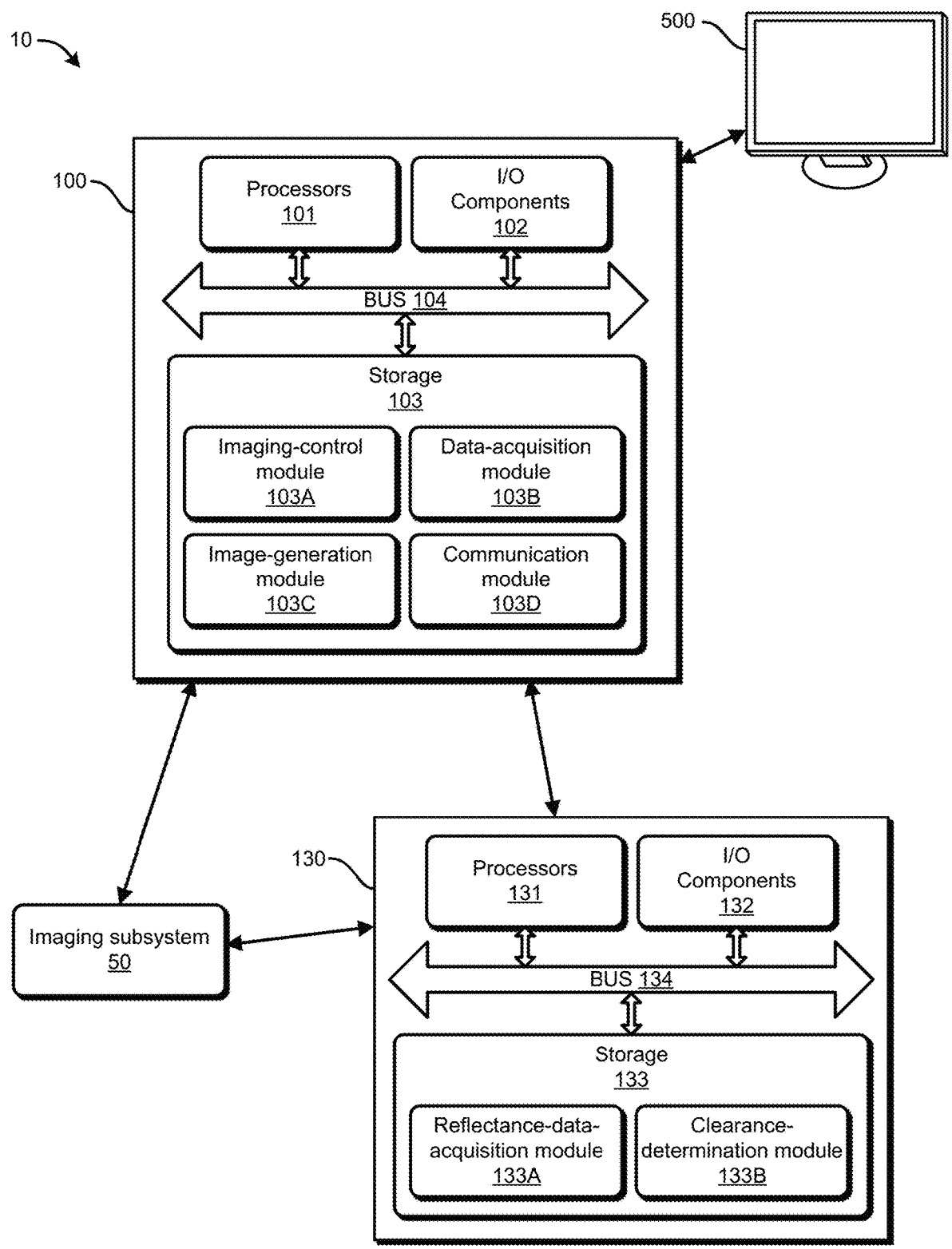
FIG. 11 illustrates an example embodiment of a medical-imaging system.

FIG. 11 illustrates an example embodiment of a medical-imaging system. The medical-imaging system 10 includes an imaging station 100, which is a specially-configured computing device; an imaging subsystem 50; a blood-clearance monitor 130; and a display device 500.

The imaging station 100 includes one or more processors 101, one or more I/O components 102, and storage 103. Also, the hardware components of the imaging station 100 communicate via one or more buses 104 or other electrical connections. Examples of buses 104 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 101 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more complex programmable logic devices (CPLDs); one or more digital signal processors (DSPs); or other electronic circuitry (e.g., other integrated circuits). The I/O components 102 include communication components (e.g., a GPU, a network-interface controller) that communicate with the display device 500, the imaging subsystem 50, the blood-clearance monitor 130, a network (not shown), and other input or output devices (not illustrated), which may include a keyboard, a mouse, a printing device, a touch screen, a light pen, an optical-storage device, a scanner, a microphone, a drive, a joystick, and a control pad.

The storage 103 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 103, which may include both ROM and RAM, can store computer-readable data or computer-executable instructions.

The imaging station 100 additionally includes an imaging-control module 103A, a data-acquisition module 103B, an image-generation module 103C, and a communication module 103D. A module includes logic, computer-readable data, or computer-executable instructions. In the embodiment shown in FIG. 11, the modules are implemented in software (e.g., Assembly, C, C++, C#, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 103. Also, in some embodiments, the imaging station 100 includes additional or fewer modules, the modules are combined into fewer modules, or the modules are divided into more modules.

The imaging-control module 103A includes instructions that cause the imaging station 100 to communicate with (e.g., send instructions to) the members of the imaging subsystem 50, to respond to clearance indicators, and to response to non-clearance indicators. For example, some embodiments of the imaging-control module 103A include instructions that cause the imaging station 100 to perform, or instruct the imaging subsystem to perform, at least some of the operations that are described in blocks B410-6420 and B470 in FIG. 4; in blocks B610, B620, B630, B650 in FIG. 6; in blocks B710, B720, B730, B740, B760, and B770 in FIG. 7; in blocks B810, B820, B830, B840, B850, B870, and B880 in FIG. 8; in blocks B910, B920, B930, B940, B950, B970, and B980 in FIG. 9; and in blocks B1010, B1020, B1030, and B1050 in FIG. 10.

The data-acquisition module 103B includes instructions that cause the imaging station 100 to obtain and record detection data (e.g., OCT-detection data, fluorescence-detection data) from the imaging subsystem 50. For example, some embodiments of the data-acquisition module 103B include instructions that cause the imaging station 100 to perform at least some of the operations that are described in block B460 in FIG. 4, in block B640 in FIG. 6, in blocks B750 and B770 in FIG. 7, in blocks B860 and B880 in FIG. 8, in blocks B960 and B980 in FIG. 9, and in blocks B1040 and B1060 in FIG. 10.

The image-generation module 103C includes instructions that cause the imaging station 100 to generate one or more images (e.g., OCT images, fluorescence images, multimodal images) based at least on obtained detection data (e.g., OCT-detection data, fluorescence-detection data). For example, some embodiments of the image-generation module 103C include instructions that cause the imaging station 100 to perform at least some of the operations that are described in block B480 in FIG. 4, in block B660 in FIG. 6, in block B780 in FIG. 7, in block B890 in FIG. 8, in block B990 in FIG. 9, and in block B1070 in FIG. 10.

The communication module 103D includes instructions that cause the imaging station 100 to communicate with other devices, such as the display device 500 and other computing devices.

Also, this embodiment of the blood-clearance monitor 130 includes one or more processors 131, one or more I/O components 132, and storage 133. The hardware components of the blood-clearance monitor 130 communicate via one or more buses 134 or other electrical connections. And the blood-clearance monitor 130 includes a reflectance-data-acquisition module 133A and a clearance-determination module 133B.

The reflectance-data-acquisition module 133A includes instructions that cause the blood-clearance monitor 130 to obtain back-reflected-excitation-light-detection data from the imaging subsystem 50. For example, some embodiments of the reflectance-data-acquisition module 133A include instructions that cause the blood-clearance monitor 130 to perform at least some of the operations that are described in blocks B430-6440 in FIG. 4, in block B605 in FIG. 6, in blocks B705 and B735 in FIG. 7, in block B805 in FIG. 8, in blocks B905 and B935 in FIG. 9, and in blocks B1005 and B1055 in FIG. 10.

The clearance-determination module 133B includes instructions that cause the blood-clearance monitor 130 to perform one or more of the following: determine whether blood clearance has been achieved or ended, based on a reflectance-detection signal; generate clearance indicators when blood clearance has been achieved; generate non-clearance indicators when blood clearance has ended; communicate with other members of the medical-imaging system 10 when blood clearance has been achieved; and communicate with other members of the medical-imaging system 10 when blood clearance has ended. For example, some embodiments of the clearance-determination module 133B include instructions that cause the blood-clearance monitor 130 to perform at least some of the operations that are described in blocks B615 and B625 in FIG. 6; in blocks B715, B725, B745, and B755 in FIG. 7; in blocks B815 and B825 in FIG. 8; in blocks B915, B925, B945, and B955 in FIG. 9; and in blocks B1015, B1025, B1035, B1045, B1065, B1075, and B1085 in FIG. 10.

Figure 12:
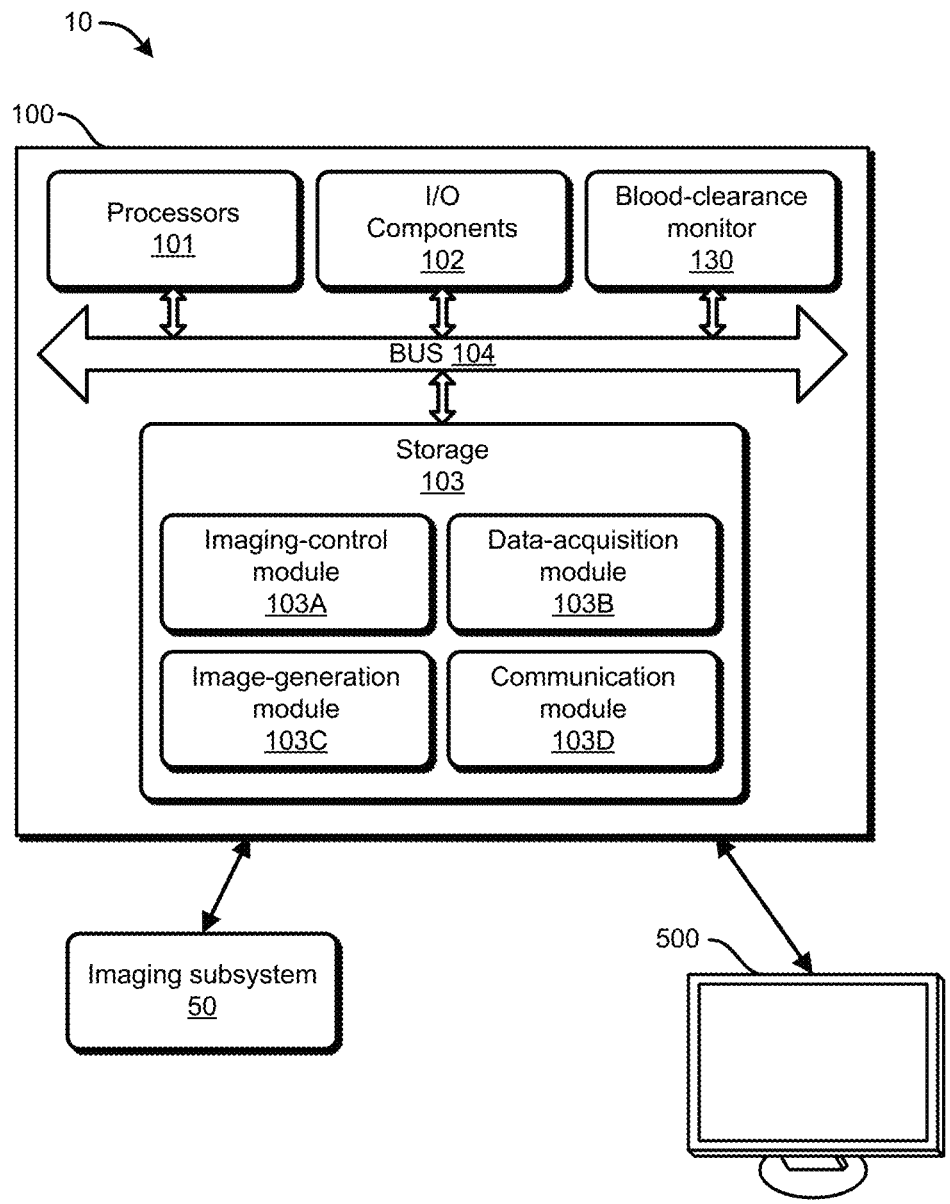
FIG. 12 illustrates an example embodiment of a medical-imaging system.

FIG. 12 illustrates an example embodiment of a medical-imaging system. The medical-imaging system 10 includes an imaging station 100, an imaging subsystem 50, a blood-clearance monitor 130, and a display device 500. In this embodiment, the blood-clearance monitor 130 is a member of the imaging station 100.

Figure 13:
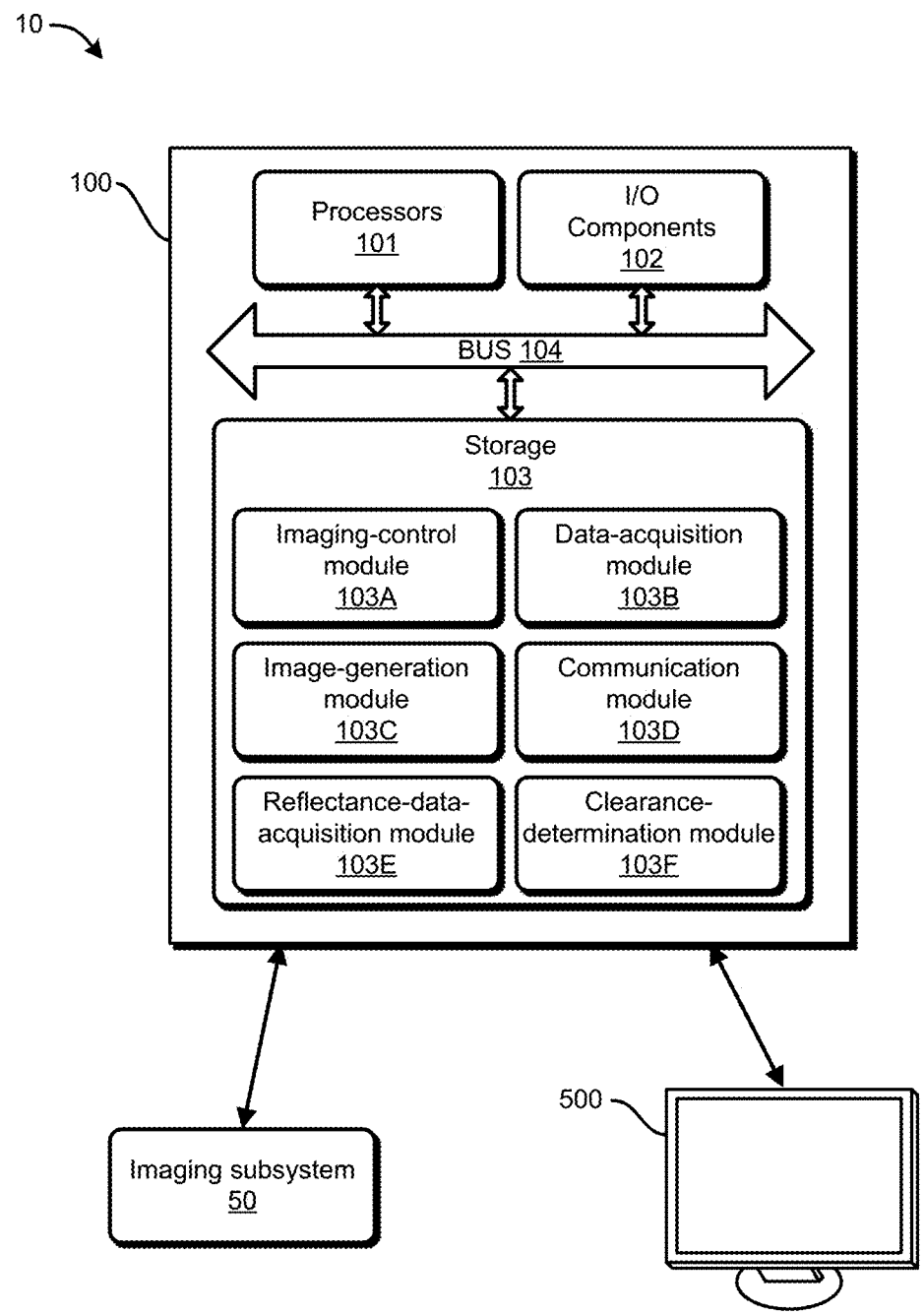
FIG. 13 illustrates an example embodiment of a medical-imaging system.

FIG. 13 illustrates an example embodiment of a medical-imaging system. The medical-imaging system 10 includes an imaging station 100, an imaging subsystem 50, and a display device 500. In this embodiment, the imaging station 100 includes a reflectance-data-acquisition module 103E and a clearance-determination module 103F. Thus, in this embodiment, the imaging station 100 implements the functionality of the blood-clearance monitor.

Figure 14:
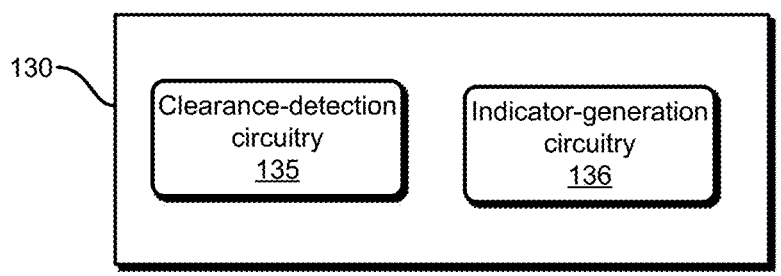
FIG. 14 illustrates an example embodiment of a blood-clearance monitor.

FIG. 14 illustrates an example embodiment of a blood-clearance monitor. This embodiment of the blood-clearance monitor includes clearance-detection circuitry 135 and indicator-generation circuitry 136. The clearance-detection circuitry 135 may include at least some of the following: analog circuits, one or more application-specific integrated circuits, and one or more microcontrollers. And the indicator-generation circuitry 136 may include at least some of the following: analog circuits, one or more application-specific integrated circuits, and one or more microcontrollers.

The clearance-detection circuitry 135 obtains back-reflected-excitation-light-detection data from the imaging subsystem 50 and determines whether blood clearance has been achieved or ended, based on a reflectance-detection signal. For example, some embodiments of the clearance-detection circuitry 135 perform at least some of the operations that are described in blocks B430-6450 in FIG. 4; in blocks B605 and B615 in FIG. 6; in blocks B705, B715, B735, and B745 in FIG. 7; in blocks B805 and B815 in FIG. 8; in blocks B905, B915, B935, and B945 in FIG. 9; and in blocks B1005, B1015, B1055, and B1065 in FIG. 10.

The indicator-generation circuitry 136 generates clearance indicators when blood clearance has been achieved, generates non-clearance indicators when blood clearance has ended, communicates with other members of the medical-imaging system 10 when blood clearance has been achieved, or communicates with other members of the medical-imaging system 10 when blood clearance has ended. For example, some embodiments of the indicator-generation circuitry 136 perform at least some of the operations that are described in block B625 in FIG. 6; in blocks B725 and B755 in FIG. 7; in block B825 in FIG. 8; in blocks B925 and B955 in FIG. 9; and in blocks B1025, B1035, B1045, B1075, and B1085 in FIG. 10.

The scope of the claims is not limited to the above-described embodiments and includes various modifications and equivalent arrangements.

The invention claimed is:
1. A medical-imaging system comprising:
a back-reflected-light detector that is configured to detect back-reflected excitation light and generate a reflectance-detection signal based on the back-reflected excitation light, wherein the back-reflected excitation light has a wavelength that is greater than or equal to 0.500 µm and less than or equal to 0.900 µm;

one or more computer-readable media storing instructions; and one or more processors that are in communication with the one or more computer-readable media and that, when executing the instructions, cooperate with the one or more computer-readable media to perform operations that comprise:

determining whether blood clearance has been achieved based on the reflectance-detection signal, and in response to determining that blood clearance has been achieved, sending, to a pullback unit, an instruction to begin a pullback procedure.

2. The system of claim 1, further comprising:

an input component configured to obtain optical-coherence-tomography-detection data from an optical-coherence-tomography detector, wherein the optical-coherence-tomography detector is configured to detect light in at least one wavelength that is used for optical-coherence-tomoqraphy imaging and generate the optical-coherence-tomography-detection data based on the detected light, wherein the operations further comprise:

in response to determining that blood clearance has been achieved, beginning recording of the optical-coherence-tomography-detection data.

3. The system of claim 2, wherein the operations further comprise:

discarding any optical-coherence-tomography-detection data, of the optical-coherence-tomography-detection data. that were obtained from the optical-coherence-tomography detector before the beginning of the recording of the optical-coherence-tomography-detection data.

4. The system of claim 2, wherein the sending of the instruction to begin the pullback procedure and the beginning of the recording of the optical-coherence-tomography-detection data are performed simultaneously or nearly simultaneously.

5. The system of claim 1, further comprising:

an input component configured to obtain fluorescence-detection data from a fluorescence detector, wherein the fluorescence detector is configured to detect fluorescence light and generate the fluorescence-detection data based on the detected fluorescence light, wherein the operations further comprise:

in response to determining that blood clearance has been achieved, beginning recording of the fluorescence-detection data.

6. The system of claim 1, wherein the operations further comprise:

in response to determining that blood clearance has been achieved, sending, to an excitation-light source, an instruction to increase a power of output excitation light such that the power of output excitation light is higher during the pullback procedure than before blood clearance has been achieved.

7. The system of claim 1, wherein the operations further comprise:

determining whether blood clearance has ended based on the reflectance-detection signal, and in response to determining that blood clearance has ended, sending, to the pullback unit, an instruction to end the pullback procedure.

8. A device for detecting blood clearance, the device comprising:

one or more electrical circuits that are configured to perform operations that comprise:

obtaining a reflectance-detection signal from a back-reflected-light detector, wherein the back-reflected-light detector is configured to detect back-reflected excitation light and generate the reflectance-detection signal based on the back-reflected excitation light, wherein the back-reflected excitation light has a wavelength that is greater than or equal to 0.500 µm and less than or equal to 0.900 µm;

determining whether blood clearance has been achieved based on the reflectance-detection signal; and issuing a clearance indicator in response to determining that blood clearance has been achieved.

9. The device of claim 8, further comprising:

the back-reflected-light detector.

10. The device of claim 8, wherein the reflectance-detection signal includes a series of intensity values, which indicate an intensity of the reflectance-detection signal over a period of time, and wherein blood clearance is determined to have been achieved when the intensity values fall beneath a threshold.

11. The device of claim 8, wherein the reflectance-detection signal includes a series of intensity values, which indicate an intensity of the reflectance-detection signal over a period of time, and wherein blood clearance is determined to have been achieved when the intensity values fall beneath a threshold and remain beneath the threshold for a set period of time.

12. The device of claim 8, wherein the operations further comprise:

in response to determining that blood clearance has been achieved, sending, to an excitation-light source, an instruction to increase a power of output excitation light such that the power of output excitation light is higher during a pullback procedure than before blood clearance has been achieved.

13. The device of claim 8, wherein the operations further comprise:

determining whether blood clearance has ended based on the reflectance-detection signal; and issuing a non-clearance indicator in response to determining that blood clearance has ended.

14. The system of claim 1, further comprising:

a fluorescence detector that is configured to detect fluorescence light;

a dichroic filter;

one or more first optical fibers that carry combined light to the dichroic filter;

one or more second optical fibers that carry fluorescence light from the dichroic filter to the fluorescence detector; and one or more third optical fibers that carry back-reflected excitation light from the dichroic filter to the back-reflected-light detector, wherein the combined light includes the fluorescence light and the back-reflected excitation light, and wherein the dichroic filter is configured to direct the fluorescence light in the combined light to the fluorescence detector via the one or more second optical fibers and direct the back-reflected excitation light in the combined light to the back-reflected-light detector via the one or more third optical fibers.

15. The system of claim 1, further comprising:

a fluorescence detector that is configured to detect fluorescence light;

an optical switch having a first position and a second position;

one or more first optical fibers that are configured to carry light to the optical switch, wherein the light includes one or both of the fluorescence light and the back-reflected excitation light;

one or more second optical fibers that are configured to carry the light from the optical switch to the fluorescence detector; and one or more third optical fibers that are configured to carry back-reflected excitation light from the optical switch to the back-reflected-light detector, wherein, in the first position, the optical switch directs the light to the back-reflected-light detector via the one or more third optical fibers, wherein, in the second position, the optical switch directs the light to the fluorescence detector via the one or more second optical fibers, and wherein the operations further comprise:
in response to determining that blood clearance has been achieved, sending, to the optical switch, a signal to change from the first position to the second position.

16. A method for medical imaging, the method comprising:

obtaining a reflectance-detection signal that was generated based on back-reflected excitation light, wherein the back-reflected excitation light has a wavelength that is greater than or equal to 0.500 μm and less than or equal to 0.900 μm;

determining whether blood clearance has been achieved based on the reflectance-detection signal; and in response to determining that blood clearance has been achieved, issuing a clearance indicator.

17. The method of claim 16, further comprising:

determining whether blood clearance has ended based on the reflectance-detection signal; and issuing a non-clearance indicator in response to determining that blood clearance has ended.

18. The method of claim 16, further comprising:

in response to determining that blood clearance has been achieved, instructing a pullback unit to begin a pullback procedure.

19. The method of claim 16, further comprising:

in response to determining that blood clearance has been achieved, instructing an excitation-light source to increase an intensity of output excitation light.

20. The method of claim 16, further comprising:

in response to the issuance of the clearance indicator, beginning recording optical-coherence-tomography-detection data that were obtained from an optical-coherence-tomography detector, wherein the optical-coherence-tomography detector is configured to detect light in at least one wavelength that is used for optical-coherence-tomography imaging and generate the optical-coherence-tomography-detection data based on the detected light.

* * * * *